United States Patent [19]
Orlek et al.

[11] Patent Number: 5,166,357

[45] Date of Patent: Nov. 24, 1992

[54] NOVEL COMPOUNDS

[75] Inventors: Barry S. Orlek; Richard E. Faulkner, both of Harlow, England

[73] Assignee: Beecham Group p.l.c., Middlesex, England

[21] Appl. No.: 418,649

[22] Filed: Oct. 10, 1989

[30] Foreign Application Priority Data

| Oct. 13, 1988 [GB] | United Kingdom | 8824071 |
| Dec. 23, 1988 [GB] | United Kingdom | 8830223 |
| Sep. 18, 1989 [GB] | United Kingdom | 8920660 |

[51] Int. Cl.$^5$ .................. A61K 31/435; C07D 471/08
[52] U.S. Cl. ..................................... 514/299; 546/112;
546/133; 548/181; 548/234; 548/235; 548/236;
548/241
[58] Field of Search ................. 546/112; 514/249

[56] References Cited

U.S. PATENT DOCUMENTS

| 4,968,691 | 11/1990 | Orlek  | 514/305 |
| 4,971,975 | 11/1990 | Hadleg | 514/299 |

FOREIGN PATENT DOCUMENTS

| 0239309 | 9/1987  | European Pat. Off. |         |
| 0257741 | 3/1988  | European Pat. Off. |         |
| 0261763 | 3/1988  | European Pat. Off. |         |
| 261763  | 3/1988  | European Pat. Off. | 548/133 |
| 0287356 | 10/1988 | European Pat. Off. |         |
| 307141  | 3/1989  | European Pat. Off. | 548/181 |
| 307142  | 3/1989  | European Pat. Off. | 548/133 |
| 0322182 | 6/1989  | European Pat. Off. |         |

OTHER PUBLICATIONS

Chem. Abs., vol. 80, No. 15, Apr. 15, 1974, E. E. Mikhlina et al.
"Synthesis . . . 2-[quinuclidinyl]-substituted imidazolines . . . " Journal of Organic Chemistry, vol. 34, No. 1, 3674–6 (1969).
D. O. Spry, "Azabicyclic Alcohols. VI. Stereospecific Syn . . . ".

*Primary Examiner*—Robert Gerstl
*Attorney, Agent, or Firm*—Hopgood, Calimafde, Kalil, Blaustein & Judlowe

[57] ABSTRACT

A compound of formula (I) or a pharmaceutically acceptable salt thereof:

in which one of X and Y represents hydrogen and the other represents Z, where Z is a group in which Q represents a 3-membered divalent residue completing a 5-membered aromatic ring and comprises one heteroatom selected from oxygen, nitrogen and sulphur or two heteroatoms selected from sulphur and nitrogen, any amino nitrogen being optionally substituted by a $C_{1-2}$alkyl, and at least one ring carbon atom being substituted by a group $R_1$; or a group in which $A_1$, $A_2$ and $A_3$ complete a 5-membered aromatic ring and $A_1$ is oxygen or sulphur, $A_2$ is $CR_2$ and $A_3$ is nitrogen or CH, or $A_2$ is oxygen or sulphur, $A_1$ is CH and $A_3$ is $CR_2$; and $R_1$ and $R_2$ are selected from, halogen, CN, $OR_4$, $SR_4$, $N(R_4)_2$, $NHCOR_4$, $NHCOOCH_3$, $NHCOOC_2H_5$, $NHOR_4NHNH_2$, $NO_2$, $COR_4$, $COR_5$, $C_{2-4}$ alkenyl, $C_{2-4}$ alkynyl or $C_{1-2}$ alkyl substituted with $OR_4$, $N(R_4)_2$, $SR_4$, $CO_2R_4$, $CON(R_4)_2$ or one, two or three halogen atoms, in which each $R_4$ is independently hydrogen or $C_{1-2}$ alkyl and $R_5$ is $OR_4$, $NH_2$ or $NHR_4$; r represents an integer of 2 or 3, s represents an integer of 1 or 2 and t represents 0 or 1, with the proviso that when Y is hydrogen s is 1.

8 Claims, No Drawings

NOVEL COMPOUNDS

This invention relates to compounds having pharmaceutical activity, to a process for their preparation and their use as pharmaceuticals.

EP0307141 published 15th Mar. 1989 discloses certain substituted 1,3-oxazoles and 1,3-thiazoles for the treatment of neurological and mental illness whose clinical manifestations are due to involvement of cholinergic neurones.

EP0307142 published 15th Mar. 1989 discloses certain substituted thiadiazoles for the treatment of neurological and mental illness whose clinical manifestations are due to involvement of cholinergic neurones.

EP0316718 published 24th May 1989 discloses certain 3-substituted quinuclidines for use in stimulating the cognitive functions of the forebrain and hippocampus of mammals including humans and in treating Alzheimer's disease.

EP0261763 published 30th Mar. 1988, EP0287356 published 19th Oct. 1988 and EP0322182 disclose azabicyclic compounds for the treatment and/or prophylaxis of dementia in mammals.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

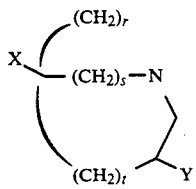

in which one of X and Y represents hydrogen and the other represents Z, where Z is a group

in which Q represents a 3-membered divalent residue completing a 5-membered aromatic ring and comprises one heteroatom selected from oxygen, nitrogen and sulphur or two heteroatoms selected from sulphur and nitrogen, any amino nitrogen being optionally substituted by a $C_{1-2}$ alkyl, and at least one ring carbon atom being substituted by a group $R_1$; or a group

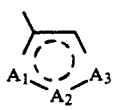

in which $A_1$, $A_2$ and $A_3$ complete a 5-membered aromatic ring and $A_1$ is oxygen or sulphur, $A_2$ is $CR_2$ and $A_3$ is nitrogen or CH, or $A_2$ is oxygen or Sulphur, $A_1$ is CH and $A_3$ is $CR_2$; and $R_1$ and $R_2$ are selected from, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, $C_{2-4}$ alkenyl, $C_{2-4}$ alkynyl or $C_{1-2}$ alkyl substituted with $OR_4$, $N(R_4)_2$, $SR_4$, $CO_2R_4$, $CON(R_4)_2$ or one, two or three halogen atoms, in which each $R_4$ is independently hydrogen or $C_{1-2}$ alkyl and $R_5$ is $OR_4$, $NH_2$ or $NHR_4$; r represents an integer of 2 or 3, s represents an integer of 1 or 2 and t represents 0 or 1, with the proviso that when Y is hydrogen s is 1. The term halogen includes bromine, chlorine and fluorine.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

In compounds of formula (I) having two asymmetric centres where Y is other than hydrogen, the stereochemical configuration in which the group Y and the $(CH_2)s$ bridge are on the same side of the plane of the molecule which contains both bridgehead atoms and the ring carbon atom bonded to the group Y will herein be referred to as the exo configuration. Similarly, the configuration of compounds in which the group Y and the bridge $(CH_2)s$ are on opposite sides of the above-mentioned plane of the molecule will herein be referred to as the endo configuration. Preferably compounds of formula (1) have the exo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (r, s, t) include (2,2,0), (3,1,0), (2,1,0), (2,1,1) and (3,1,1). Examples of combinations of (r, s, t) include (3,1,0), (2,2,0) and (2,1,0).

Y is preferably hydrogen.

5-Membered aromatic heterocycles within the definition of variable Z include oxazole such as 1,3-oxazol-4-yl, 1,3-oxazol-5-yl and 1,2-oxazol-3-yl, and thiazole such as 1,3-thiazol-4-yl.

Examples of $R_1$ and $R_2$ include $NH_2$, $CH_2F$, $CO_2CH_3$, $CH_2OH$, $CH_2OCH_3$, CN, $NHCOCH_3$ and $NHCH_3$.

Preferred values for $R_1$ and $R_2$ include $NH_2$, $CH_2F$, $CH_2OH$ and $CH_2OCH_3$.

Subgroups of the compounds of formula (I) include the following:

(i) Z is a 1,3-oxazolyl or 1,3-thiazolyl group substituted by $CH_2F$;
(ii) Z is a 1,3-oxazolyl or 1,3-thiazolyl group substituted by $NHCH_3$;
(iii) Z is a 1,3-oxazolyl or 1,3-thiazolyl group substituted by $NHCOCH_3$;
(iv) Z is a 1,3-oxazolyl or 1,3-thiazolyl group substituted by $CH_2OCH_3$;
(v) Z is a 1,3-oxazolyl or 1,3-thiazolyl group substituted by $CH_2OH$;
(vi) Z is a 1,3-oxazolyl or 1,3-thiazolyl group and (r,s,t) is (3,1,0) or (2,1,1);
(vii) Z is a 1,3-oxazol-5-yl group;
(viii) Z is a 2-amino-1,3-oxazol-5-yl group;
(ix) Z is a 1,3-oxazolyl group and (r,s,t) is (2,1,0);
(x) Z is a 2-amino-1,3-oxazolyl group and (r,s,t) is (2,1,0);
(xi) Z is a 1,2-oxazol-3-yl group;

(xii) compounds of any of subgroups (i) to (vi) where Z is a 1,3-oxazol-5-yl group;
(xiii) compounds of any of subgroups (i) to (vi) where Z is a 1,3-oxazol-4-yl group;
(xiv) compounds of any of subgroups (i) to (vi) where Z is a 1,3-thiazol-4-yl group;
(xv) compounds of any of subgroups (i) to (vi) where Z is a 1,2-oxazol-3-yl group;
(xvi) Z is other than 1,3-oxazolyl, 1,3-thiazolyl, 1,2,4-thiadiazolyl or 1,3,4-thiadiazolyl;
(xvii) Q comprises one nitrogen atom, $A_1$ is oxygen or sulphur, $A_2$ is $CR_2$ and $A_3$ is CH or $A_2$ is oxygen or sulphur, $A_1$ is CH and $A_3$ is $CR_2$;
(xviii) compounds of any of subgroups (i) to (xvii) where X is hydrogen;
(xix) compounds of any of subgroups (i) to (xvii) where Y is hydrogen.

It will be appreciated that the range of values for $R_1$ and $R_2$ will be limited by the preparative constraints and/or stability of the group Z. For example, a 1,3-oxazole ring will tolerate a 2-amino substituent whereas 2-amino furans are unstable. Conversely, 2-halo-furans are stable whereas 2-halo-1,3-oxazoles are very labile compounds.

Examples of Z are 2-amino-1,3-oxazol-4-yl, 2-amino-1,3-oxazol-5-yl, 2-amino-1,3-thiazol-4-yl, 2-fluoromethyl-1,3-oxazol-5-yl, 2-methoxycarbonyl-1,3-oxazol-5-yl, 2-hydroxymethyl-1,3-oxazol-5-yl, 2-methoxymethyl-1,3-oxazol-5-yl, 2-cyano-1,3-oxazol-5-yl, 2-methylcarbonylamino-1,3-oxazol-5-yl and 2 methylamino-1,3-oxazol-5-yl.

The invention also provides a process for the preparation of a compound of formula (I), or a pharmaceutically acceptable salt thereof, which process comprises:
(a) cyclising a compound of formula (II):

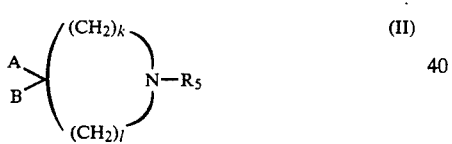

(II)

in which
(i) A represents Z or a group convertible thereto and B represents $-(CH_2)_jL_1$ where $L_1$ is a leaving group or A and $L_1$ together represent $-COO-$; one of j, k and l is 1 and the other two independently represent an integer of 2 or 3, and $R_5$ represents hydrogen or an N-protecting group; to give a compound of formula (IIa):

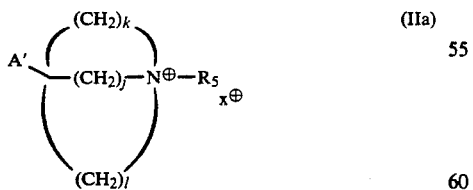

(IIa)

in which A' represents Z or a group convertible thereto, $x^-$ is an anion and the remaining variables are as previously defined;
or (ii) A represents an electron withdrawing group, B represents hydrogen and $R_5$ represents $-(CH_2)_jL_2$ where $L_2$ is a leaving group; one of k and l is 1 and the other and j independently represent an integer of 2 or 3; to give a compound of formula (IIb):

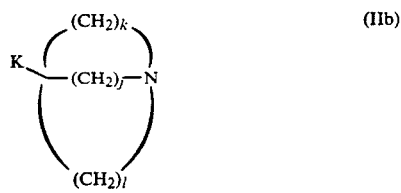

(IIb)

in which K represents an electron withdrawing group or A' and the remaining variables are as previously defined; and thereafter, optionally or as necessary and in any appropriate order, removing any $R_5$ N-protecting group, converting K to A', converting A' to Z, optionally interconverting Z and/or forming a pharmaceutically acceptable salt; or
(b) cyclising a compound of formula (III):

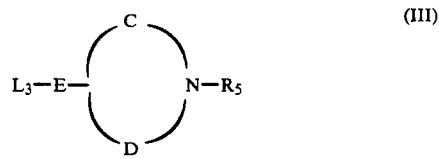

(III)

where $R_5$ is hydrogen or an N-protecting group, and either C is one, D is another and E is the remainder of $-(CH_2)_r-$, $-(CH_2)-$ and $-(CH_2)_r-$CHA'$-CH_2-$ or groups convertible thereto, A' is Z or a group convertible thereto and $L_3$ is a leaving group; or C is one and E is the other of $-(CH_2)_r-$ and $-(CH_2)_s-$ or groups convertible thereto and D represents $-(CH_2)_r-$CHA'$-CH_2-$ where A' and $L_3$ together represent $-COO-$, and thereafter, optionally or as necessary and in any appropriate order, converting C, D and E to $-(CH_2)_r-$, $-(CH_2)_s-$ and $-(CH_2)_r-$CHA'$-CH_2-$, removing any $R_5$ protecting group, converting A' to Z, optionally interconverting Z and/or forming a pharmaceutically acceptable salt; or
(c) cyclising a compound of formula (IV):

(IV)

where F is one and G is the other of $-(CH_2)_r-$ and $-(CH_2)_s-$ or groups convertible thereto, and one of $Y^3$ and $Y^4$ is $-(CH_2)_u-$K and the other is $-(CH_2)_v(CO)_yL_4$ where K is an electron withdrawing group, $L_4$ is a leaving group, u is 1 or 2 and v and y are independently 0 or 1, with the proviso that when $Y_4$ is $-(CH_2)_v(CO)_yL_4$, v and y are 1, u, v and y being such that the desired compound of formula (I) is obtained, and thereafter, optionally or as necessary and in any appropriate order, hydrolysing and decarboxylating the cyclisation product and converting the carbonyl group to CHA' where A' is Z or a group convertible thereto, converting K to A' as defined, converting A' to Z, converting F and G to $-(CH_2)_r-$ and —$(CH_2)_s$—as appropriate, interconverting Z and-/or forming a pharmaceutically acceptable salt.

It will be appreciated that the product of process variant (a) is a compound of formula (I) in which variable Y is hydrogen and that the product of process variant (b) or (c) is a compound of formula (I) in which variable X is hydrogen.

In process variant (a), examples of the leaving groups $L_1$ and $L_2$ include halo such as bromo, tosyloxy and mesyloxy.

Examples of $R_5$ when an N-protecting group include benzyl and substituted benzyl.

Examples of A and A' include alkoxycarbonyl, benzyloxycarbonyl and cyano.

The cyclisation reaction is a nucleophilic substitution which may be carried out under conventional conditions appropriate to the groups A and B. Thus, when B is $(CH_2)_jBr$ and A is $C_{1-4}$ alkoxycarbonyl, the cyclisation is carried out in an inert solvent such as toluene or ether at elevated temperature. When B is $(CH_2)_jOTos$ or $(CH_2)_jO$-Mes, it is preferably obtained by treatment of a $(CH_2)_jOH$ group with a suitable reagent such as tosylchloride or mesyl chloride, in a base such as pyridine, whereupon the cyclisation may proceed at ambient temperature, or at elevated temperature in an inert solvent such as toluene. When A and $L_1$ together represent —COO—, the cyclisation may be carried out in a lower alkanol such as ethanol in the presence of acid such as hydrogen bromide. In the resulting compound of formula (IIa), A' will be an alkoxycarbonyl group corresponding to the lower alkanol used for the cyclisation.

Where $R_5$ is an N-protecting group such as benzyl, this may be removed by conventional hydrogenation, preferably catalytically over a suitable catalyst such as Pd/C. Where A' or K is benzyloxycarbonyl, deesterification and deprotection may be effected simultaneously by conventional hydrogenation.

Examples of K and A when an electron withdrawing group include $C_{1-4}$ alkoxycarbonyl and cyano.

When A is an electron withdrawing group such as $C_{1-4}$ alkoxycarbonyl, B is hydrogen and $R_5$ is —$(CH_2)_jL_2$ where $L_2$ is, for example, chloro, the cyclisation may be effected by treatment of the compound of formula (II) with lithium diisopropylamide.

In process variant (b), examples of leaving groups $L_3$ include halo such as chloro and hydroxy. In the group —$(CH_2)_r$—CHA'—$CH_2$—, examples of A' include hydroxy, $C_{1-4}$ alkoxycarbonyl and cyano. Examples of groups convertible to —$(CH_2)_r$—CHA'—$CH_2$—include —$(CH_2)_r$—CO—$CH_2$. In process variant (c), examples of $L_4$ include those given for $L_3$ or $C_{1-4}$ alkoxy such as ethoxy. Examples of electron withdrawing groups K include $C_{1-4}$ alkoxycarbonyl and cyano.

In process variant (b), where $L_3$ is hydroxy and D is —$(CH_2)_r$—CHOH—$CH_2$—, the cyclisation of compounds of formula (III) may be carried out by pyrolysis, by the method of D. O. Spry and H. S. Aaron, J. Org. Chem., 1969, 34, 3674, to yield a compound where A' is hydroxy.

Where E is —$(CH_2)_r$—CO—$CH_2$—, the cyclisation may be carried out under basic conditions where $R_5$ is benzyl (F. I. Carrol, A. M. Ferguson, and J. B. Lewis, J. Org. Chem. 31, 2957, 1966). The resulting ketone may be reacted with tosylmethyl isocyanide to yield a compound where A' is cyano.

Where $L_3$ and A' together represent —COO—, the cyclisation is a rearrangement reaction which can be carried out under acid conditions in a polar solvent, such as hydrogen bromide in ethanol, at ambient temperature, to yield a compound where A' is a carboxy ester group. It is preferred to protect the nitrogen atom with an $R_5$ N-protecting group such as benzyl, which may be subsequently removed by hydrogenation over a suitable catalyst such as Pd/C.

In process variant (c), where $Y^3$ and $Y^4$ both contain carboxy ester groups the cyclisation of compounds of formula (IV) is a Dieckmann reaction which is catalysed by a base such as potassium t-butoxide at elevated temperature in a solvent such as toluene.

The resulting $\beta$-keto ester is hydrolysed and decarboxylated under conventional conditions such as heating at reflux in dilute hydrochloric acid.

The carbonyl group may be reduced to an A' hydroxy group with a suitable reducing agent such as sodium borohydride in ethanol at ambient temperature, or sodium in ethanol at elevated temperature, such as the boiling point of the solvent, under an inert atmosphere such as nitrogen, depending on the stereochemistry required.

An A' hydroxy group may be converted to cyano by first converting it to a good leaving group such as mesyloxy or tosyloxy and then displacing it with cyanide ion.

Alternatively, the carbonyl group may be converted directly to an A' cyano group with a suitable reagent such as tosylmethylisocyanide in an inert solvent such as dry dimethoxyethane, at depressed temperature, under basic conditions such as in the presence of potassium t-butoxide.

Where y is 0, the cyclisation may be carried out as described in EP-0094742 under basic conditions such as sodium hydride and potassium t-butoxide, in an inert polar solvent such as dimethylformamide.

Conversions of groups A' and K, and interconversions of Z, may be carried out conventionally, see for example standard text books on heterocyclic chemistry such as 'Comprehensive Heterocyclic Chemistry', A. R. Katritzky and C. W. Rees, Pergamon, 1984.

The A' or K group is first converted, as necessary, to a suitable starting group Z' for the chosen conversion reaction to give the required group Z.

A Z' carboxy group may be obtained by conventional de-esterification of an A alkoxycarbonyl group.

A Z' chlorocarbonyl group may be obtained by treatment of a Z' carboxy group with thionyl chloride at elevated temperature.

An A' hydroxy group may be oxidised to a carbonyl group by treatment with chromic acid or using dimethyl sulphoxide and dicyclohexylcarbodiimide.

A Z' aminocarbonyl group may be obtained by treatment of a Z' chlorocarbonyl group with ammonia.

A Z' cyano group may be obtained by treatment of a Z' aminocarbonyl group with a dehydrating agent such as phosphorus pentoxide in toluene, or pyridine and trifluoroacetic anhydride.

A Z' $CH_3CO$—group may be obtained by treatment of a LiOOC group with methyl lithium, the LiOOC group being obtained by hydrolysis of an A' alkoxycarbonyl group with lithium hydroxide in water. Alternatively, a Z' $CH_3CO$—group may be obtained by reaction of a Z' chlorocarbonyl group with N,O-dimethylhydroxylamine and treatment with methyl lithium. A Z' $CH_3CO$—group may also be obtained by treatment of a cyano group with methyl lithium.

A Z' bromomethylcarbonyl group may be obtained by treatment of a Z' $COCH_3$ group either with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively, a Z' —COCl group may be converted to a —COCH$_2$Br group by treatment with diazomethane in ether at low temperature followed by hydrogen bromide in acetic acid at ambient temperature.

When Z represents 2-amino-1,3-oxazol-4-yl, a Z' bromomethylcarbonyl group may be reacted with urea, either in the absence of solvent or in the presence of a solvent such as N,N-dimethylformamide, at elevated temperature, for example in the range 110°–160° C., the nitrogen atom of the azabicycle being protected, suitably as the hydrobromide salt.

When, Z represents 2-amino-1,3-thiazol-4-yl, a Z' bromomethylcarbonyl group may be reacted with thiourea in place of urea, as described above. Typically, the temperature used for the reaction is in the range 110°–160° C. At the higher end of this range the formyl derivative of the required 2-amino-1,3-thiazol-4-yl group may be produced. Subsequent hydrolysis under basic or acidic conditions can then be used to obtain the required amino compound.

When Z represents 2-amino-1,3-oxazol-5-yl, a Z' bromomethylcarbonyl group may be converted to cyanamidomethylcarbonyl by reaction with sodium cyanamide in a solvent such as N,N-dimethylformamide, which may be cyclised under basic conditions such as when subjected to chromatography using basic alumina.

When Z represents 2-($C_{1-2}$ alkoxycarbonyl)-1,3-oxazol-5-yl, a Z' bromomethylcarbonyl group may be converted to aminomethylcarbonyl by treatment with NaN$_3$ in acetone or N,N-dimethylformamide followed by hydrogenation over a Pd/C catalyst in ethanolic HCl, or by treatment with hexamethylene tetramine followed by hydrolysis in methanolic HCl. The aminomethylcarbonyl group may then be treated with $C_{1-2}$ alkoxyoxalyl chloride and the product cyclised either in the presence of excess reagent or using a suitable dehydrating agent such as polyphosphoric acid at elevated temperature.

Where a 2-alkoxymethyl-1,3-oxazol-5-yl group is required, an aminomethylcarbonyl group may be acylated with the appropriate alkoxyacetyl chloride to give the intermediate acyl amino ketone which may be cyclised as described in the preceding paragraph.

A 2-fluoromethyl-1,3-oxazol-5-yl group may be obtained by treatment of an aminomethylcarbonyl group with a suitable mixed anhydride of monofluoroacetic acid, for example that derived from reaction with isobutylchloroformate, and the intermediate acyl amino ketone cyclised as previously described.

When Z represents 5-amino-1,2-oxazol-3-yl, a Z' cyanomethylcarbonyl group may be reacted directly with hydroxylamine hydrochloride followed by cyclisation under acid conditions.

Interconversion of carbon substituents R$_1$ and R$_2$ within a group Z may be carried out conventionally. Thus an amino group may be converted to chloro, or —NHNH$_2$, via a diazonium intermediate. Similarly a chloro substituent may be converted by reaction with a nucleophile such as methoxide; and alkoxycarbonyl groups may be converted, via carboxy, to an amino substituent. Alkoxycarbonyl groups may be converted via aminocarbonyl to cyano and may be reduced to hydroxymethyl using a suitable reducing agent such as lithium borohydride or diisobutylaluminium hydride.

Hydroxymethyl groups may be converted, via halomethyl such as chloromethyl by treatment with a suitable reagent such as thionyl chloride, to alkoxymethyl by treatment with the appropriate sodium alkoxide. Substituted amino groups may be obtained by substitution of the primary amine with the appropriate moiety.

Where applicable, an endo isomer may be obtained by epimerisation of a corresponding exo isomer, the epimerisation reaction being effected by standard procedures at any convenient stage in the process but preferably before the introduction of the group Y.

Compounds of formula (II) may be prepared conventionally.

Where A is $C_{1-4}$ alkoxycarbonyl, B is (CH$_2$)$_j$L$_1$ and R$_5$ is hydrogen or an N-protecting group, the compound of formula (II) may be prepared by treating a compound of formula (V):

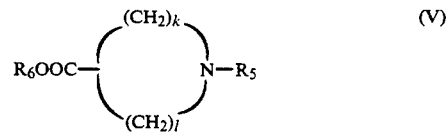

(V)

where R$_6$ is $C_{1-4}$ alkyl and the remaining variables are as previously defined, with lithium diisopropylamide, prepared in situ from diisopropylamine and n-butyllithium followed by reaction with a compound L$_5$(CH$_2$)$_j$L$_1$ where L$_5$ is a leaving group, in an inert solvent such as ether at depressed to elevated temperature. Both L$_1$ and L$_5$ are suitably bromo.

Where A and L$_1$ together represent —COO—and j is 2, the compound of formula (II) may be prepared by reacting the compound of formula (V), treated with lithium diisopropylamide as before, with ethylene oxide in an inert solvent such as ether at depressed to elevated temperature.

Alternatively, the compound of formula (II) where A and L$_1$ together represent —COO, j is 2, k is 2 and l is 1 may be prepared by a 1,3-dipolar cycloaddition reaction which involves reacting a compound of formula (VI):

(VI)

with a compound of formula (VII):

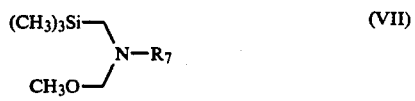

(VII)

in which R$_7$ is an N-protecting group in the presence of a catalytic amount of trifluoroacetic acid.

Where A is an electron withdrawing group such as $C_{1-4}$ alkoxycarbonyl, B is hydrogen and R$_5$ is (CH$_2$)$_j$L$_2$, the compound of formula (II) may be prepared by reacting the compound of formula (V) where R$_5$ is hydrogen with a compound L$_5$(CH$_2$)$_j$L$_2$ where L$_5$ is as previously defined, in a solvent such as acetone in the presence of a base such as potassium carbonate. The leaving group $L_5$ is preferably bromo and $L_2$ is preferably chloro.

Compounds of formulae (V) are known compounds or may be prepared by analogous methods to those for preparing known compounds. The compound of formula (V) where k is 2, l is 1 and $R_5$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Intermediates of formulae (III) and (IV) are known compounds (e.g. as described in EP-A-0094742 or EP-A-0261763) or may be prepared analogously.

Intermediates of formula (III) where A' and $L_3$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (III) where $L_3$ is a leaving group are described in, for example, Spry et al., J. Org. Chem., 1969, 34, 3674 and Hasse et al., Chem. Ber., 1960, 93, 1686.

Intermediates of formula (IV) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Compounds of formulae (VI) and (VII) may be prepared conventionally. Thus, a compound of formula (VI) may be obtained by the reaction of γ-butyrolactone with ethyl formate in the presence of base such as sodium hydride followed by reaction of the resulting formyl derivative (as the enol salt) with formaldehyde. A compound of formula (VII) may be obtained by the reaction of the primary amine $R_7NH_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia. In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) Ethyl 1-(2-chloroethyl)-3-piperidylcarboxylate (D1)

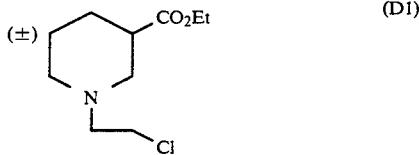

A solution of ethyl 3-piperidylcarboxylate (100g, 0.64 mole) in acetone (800ml) was treated with 1-bromo-2-chloroethane (106.5ml, 1.28 mole) and anhydrous potassium carbonate (138g, 1.00 mole) and the mixture stirred at room temperature for 24h. The mixture was concentrated in vacuo and the residue treated with water (300ml) and extracted with ether (2 ×200ml). The combined ether extracts were dried (Na$_2$SO$_4$) and concentrated in vacuo to leave a yellow oil, which was purified by chromatography on silica gel eluting with 50% ether/60-80 petrol to give the title compound (D1) as a pale yellow oil (78.2g, 56%).

$^1$H Nmr (CDCl$_3$) δ: 1.25 (3H, t, J=7Hz), 1.40-3.10 (11H, m), 3.58 (2H, t, J=7Hz), 4.15 (2H, q, J=7Hz).

DESCRIPTION 2

(±) Ethyl 1-azabicyclo[3.2.1]oct-5-ylcarboxylate (D2)

A solution of diisopropylamine (33.6ml, 0.24 mole) in dry ether (1500 ml) at −65° C. under nitrogen was treated with 1.5M n-butyllithium in hexane (150 ml, 0.225 mole) and the solution stirred for 15 min, before adding N,N,N',N'-tetramethylethylenediamine (68 ml, 0.45 mole). After stirring for a further 15 min, the solution was treated with a solution of ethyl 1-(2-chloroethyl)-3-piperidylcarboxylate (D1, 44.7g, 0.204 mole) in dry ether (100 ml) and the mixture allowed to warm up to room temperature over 2h. The reaction mixture was treated with potassium carbonate solution (300 ml) and the ether layer separated, dried (Na$_2$SO$_4$) and concentrated in vacuo to leave an orange oil. This was purified by chromatography on silica gel eluting with 10% methanol/chloroform to give the title compound (D2) as a yellow oil (31.9g, 84%), b.p. 120°-130° C. at 0.4 mm (Kugelröhr apparatus).

$^1$H Nmr (CDCl$_3$) δ: 1.25 (3H, t, J=7Hz), 1.10-2.20 (6H, m), 2.60-3.25 (6H, m), 4.20 (2H, q, J=7Hz).

DESCRIPTION 3

(±) 1-Azabicyclo[3 2.1]oct-5-yl-N-methyl-N-methoxycarboxamide (D3)

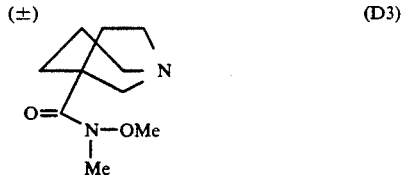

A solution of (±) ethyl 1-azabicyclo[3.2.1]oct-5-ylcarboxylate (D2) (40.0g; 0.22 mole) in 5N hydrochloric acid (300 ml) was heated under reflux for 2h. The reaction mixture was concentrated in vacuo to give a crystalline solid which was treated with excess thionyl chloride (200 ml) and warmed to reflux over 10 min. Heating at reflux was continued for 20 min, at which point the copious evolution of hydrogen chloride and sulphur dioxide ceased. The reaction was concentrated in vacuo and repeated codistillation with dry toluene was used to remove residual thionyl chloride. The crude acid chloride was dissolved in dry dichloromethane (300ml) and treated at 0° C. with N,O-dimethylhydroxylamine hydrochloride (23.47g; 0.24 mole) and pyridine (87.0g; 1.1 mole). The reaction was allowed to warm slowly to room temperature, and stirring was continued for 12h. A saturated solution of potassium carbonate was added and after separation of the organic phase the aqueous layer was extracted into chloroform. The combined organic layers were dried over sodium sulphate and concentrated in vacuo. Distillation afforded the title compound (D3) as a colourless oil (35.3g; 81%), bp 120°-130° C. at 0.5 mmHg. On standing the product solidified, m.p. 38°-40° C.

DESCRIPTION 4

(±) 5-Acetyl-1-azabicyclo[3.2.1]octane (D4)

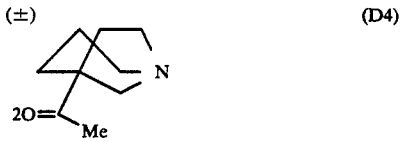

A solution of (±) 1-azabicyclo[3.2.1]oct-5-yl-N-methyl-N-methoxycarboxamide (D3) (22.0g; 0.11 mole) in dry ether (500 ml) was cooled to −30° C. under nitrogen and treated dropwise with methyl lithium (80.0 ml of a 1.4 M solution in diethyl ether; 0.11 mole). The rate of addition was controlled to ensure that the temperature of the reaction remained below 0° C. After stirring for 1 h at −10° C. the reaction was quenched by the addition of excess glacial acetic acid, while maintaining the temperature below −10° C. The ether solution was washed with a solution of saturated potassium carbonate. After extraction of the aqueous phase with chloroform (3×200ml) the combined organic layers were dried over sodium sulphate and concentrated in vacuo. Distillation afforded the title compound (D4) (15.0g; 88%), bp 150° C. at 0.4 mmHg.

1H Nmr (CDCl3) δ: 1.45-1.55 (1H, m), 1.65-1.90 (4H, m), 2.00-2.10 (1H, m), 2.15 (3H, s), 2.65-3.00 (5H, m), 3.05-3.20 (1H, m).
Ir (film) υC=O 1695cm⁻¹.

DESCRIPTION 5

(±) 5-(α-Bromoacetyl)-1-azabicyclo[3.2.1]octane hydrobromide (D5)

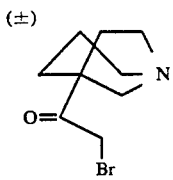
(D5)

A solution of the hydrobromide salt of (±) 5-acetyl-1-azabicyclo[3.2.1]octane (D4) (2.0g; 8.5 mmole) in dry methanol (35ml) was cooled to −10° C. and treated with a solution of bromine (0.44ml; 8.5 mmole) in dry methanol (5ml). The reaction was maintained at 0° C. for 18h. A further quantity of bromine (0.44 ml) was added and after 5h at room temperature the reaction was diluted with water and stirred for 1h. Evaporation of solvent and excess reagent in vacuo afforded a yellow foam (3.0 g) consisting mainly of the title compound (D5). This material was used in the next stage without purification.
Ir (film) υC=O 1720 cm⁻¹.

DESCRIPTION 6

(±) 3-Acetyl-1-azabicyclo[2.2.2]octane (D6)

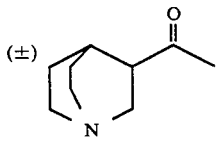
(D6)

To a solution of (±) 3-cyano-1-azabicyclo[2.2.2]octane (EP 0261763 D1) (10.0 g; 0.07 mole) in dry ether (125 ml) cooled to 0° C. under nitrogen was added methyl lithium (67 ml of a 1.5 M solution in ether; 0.10 mole) over 15 min. After 2h at 0° C. the reaction was quenched with 125 ml of 5N sulphuric acid and stirred for a further 3h at ice temperature. After separation of the ether layer, the aqueous phase was saturated with potassium carbonate and extracted into chloroform (4×100 ml). The combined extracts were dried (Na2SO4) and concentrated in vacuo to give 11.5g of crude ketone. Purification on neutral alumina using ethyl acetate-cyclohexane (1:1) as eluant afforded the title compound (D6) as a colourless oil which solidified on cooling (7.0 g; 64%).

DESCRIPTION 7

(±) 3-(α-Bromoacetyl)-1-azabicyclo[2.2.2]octane hydrobromide (D7)

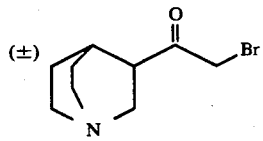
(D7)

Hydrogen bromide gas was bubbled through an ice cooled solution of (±) 3-acetyl-1-azabicyclo[2.2.2]octane (D6) (5.3g; 0.035 mole). After decanting off the supernatant liquid, the hydrobromide salt was dried in vacuo, then dissolved in dry methanol (125 ml) and cooled in ice. Hydrogen bromide gas was bubbled gently into the solution for approx. 5 min, and the solution was then treated with bromine (5.5g; 0.035 mole in 10ml methanol). The reaction was allowed to warm to room temperature, and after 24h a further portion of bromine (2.7g; 0.017 mole) was added. Stirring was continued for a further 24h. The solution was cooled in ice, diluted with water (100 ml), and allowed to warm to room temperature over 1 h. The mixture was concentrated in vacuo. while maintaining the temperature below 40° C. Repeated co-evaporation with toluene was used to remove residual water. Subsequent trituration with ethermethanol afforded the title compound (D7) (7.28g; 65%) as a crystalline solid which was used directly in the next stage.

DESCRIPTION 8

(±) Methyl 1-benzyl-2-oxo-4-pyrrolidylcarboxylate (D8)

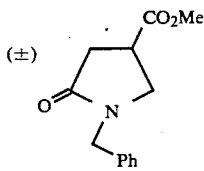
(D8)

A solution of dimethyl itaconate (50g, 0.32mole) in methanol (40 ml) was treated with benzylamine (34.6 ml, 0.32mole) and the mixture heated under reflux for 2.5h. The solution was then concentrated in vacuo and the residue purified by distillation (b.p. 162°-170° C./0.2 mmHg) to give a pale yellow oil. This solidified on standing to give the title compound (D8) as a beige solid (66.2g, 89%), m.p. 62°-63° C.

DESCRIPTION 9

(±) Methyl 1-benzyl-3-pyrrolidylcarboxylate (D9)

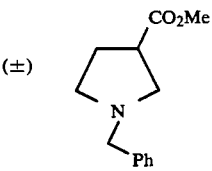
(D9)

A solution of (±) methyl 1-benzyl-2-oxo-4-pyrrolidylcarboxylate (D8, 35.4g, 0.18mole) in dry THF (135 ml) was added dropwise over 30 mins to 1M borane-THF solution (228ml, 0.23mole) at 0° C. under nitrogen, and when addition was complete the solution was heated under reflux for 1 h. The solution was cooled to room temperature, then treated dropwise with 8% hydrogen chloride/methanol (114 ml, 0.25 mole HCl) and stirred for 18 h, followed by 3h at reflux. The mixture was then concentrated in vacuo and the residue treated with water (40ml), washed with ether (2×50ml), basified with 40% sodium hydroxide solution, saturated with potassium carbonate and extracted with ether (3×70 ml). The combined extracts were dried (Na2SO4) and concentrated in vacuo to leave a yellow oil, which was purified by distillation (b.p. 146° C./0.7 mmHg) to give the title compound (D9) as a colourless oil (19.8g, 50%).

DESCRIPTION 10

N-Benzyl-N-[(trimethylsilyl)methyl]amine (D10)

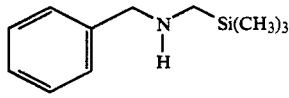
(D10)

A mixture of chloromethyltrimethylsilane (325g, 370 ml, 2.65 mole) and benzylamine (835 g, 850 ml, 7.78 mole) was heated at 120° C. (oil bath temperature) for 2 h. A white solid began appearing after only 10 minutes and a viscous mixture eventually resulted. The reaction mixture was allowed to cool, then basified with potassium carbonate solution and extracted twice with ether. The combined extracts were dried ($Na_2SO_4$) and concentrated in vacuo to leave a yellow oil, which was purified by distillation. The excess benzylamine was removed in the first fractions (b.p. 47°-62° C. at 2 mmHg). The title compound (D10) was obtained as a colourless oil (380 g, 74%) b.p. 75°-80° C. at 2 mmHg.

$^1$H NMR ($CDCl_3$) δ: 0.10 (9H, s), 1.40 (1H, br.s, NH), 2.10 (2H, s), 3.85 (2H, s), 7.27-7.43 (5H, m)

DESCRIPTION 11

N-Benzyl-N-(methoxymethyl)-N-[(trimethylsilyl)methyl]amine (D11)

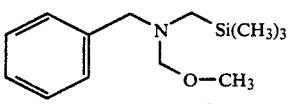
(D11)

A stirred 37% aqueous formaldehyde solution (230 g, 215 ml, 2.8 mole) was cooled to −5° C. and treated dropwise over 20 minutes with N-benzyl-N-[(trimethylsilyl)methyl]amine (D10, 380 g, 1.96 mole), whilst keeping the temperature between −5 and 0° C. After completing the addition, the mixture was treated with methanol (230 ml), saturated with potassium carbonate and stirred at room temperature for 2h. The mixture was treated with ether (500ml) and the organic phase separated, dried ($K_2CO_3$) and concentrated in vacuo to give a colourless oil (480 g), which was about 75% title compound (D11). This material was used in the next stage without purification.

$^1$H NMR ($CDCl_3$) δ: 0.10 (9H, s), 2.23 (2H, s), 3.30 (3H, s), 3.82 (2H, s), 4.05 (2H, s), 7.25-7.40 (5H, m)

DESCRIPTION 12

α-Formyl-γ-butyrolactone sodium salt (D12)

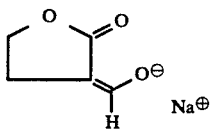
(D12)

A stirred suspension of sodium hydride (300g of 80% oil dispersion, 10 moles) in dry ether (8l) under nitrogen was treated slowly with absolute ethanol (60ml, 1.1 mole), followed immediately by a mixture of ethyl formate (808 ml, 10 moles) and Y-butyrolactone (770ml, 10 moles) over about 1.25h. The rate of addition of the reagents was regulated to give a steady reflux and evolution of hydrogen (about 220l). After completing the addition, the mixture was stirred for a further 0.5h and the solid then filtered off, washed with ether and dried in vacuo to give the title compound (D12) as a white solid (1.32kg, 97%).

DESCRIPTION 13

α-Methylene-γ-butyrolactone (D13)

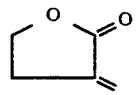
(D13)

A stirred suspension of paraformaldehyde (270g, 9.0 mole) in THF (3.5L) at room temperature in a 20L flask under nitrogen was treated with α-formyl-γ-butyrolactone sodium salt (D12, 270g, 2.0 mole). The mixture was then immediately heated to reflux temperature for 1h. Evolution of a small quantity of gas was observed. The mixture was cooled to around 10° C., treated with saturated aqueous potassium carbonate solution (500ml) and ether (1.5L), and the organic layer separated, dried ($Na_2SO_4$) and concentrated in vacuo to leave a pale yellow oil. This material was distilled to give the title compound (D13) as a colourless oil (125g, 64%) b.p. 76°-80° C. at 8 mmHg.

$^1$H NMR ($CDCl_3$) δ: 2.95-3.03 (2H, m), 4.40 (2H, t, J TM 7Hz), 5.69 (1H, t, J=3Hz), 6.25 (1H, t, J=3Hz)

DESCRIPTION 14

(±) 7-Benzyl-7-aza-2-oxaspiro[4.4]nonan-1-one (D14)

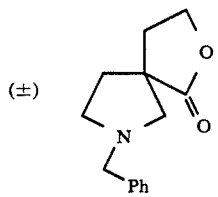
(D14)

Method A

A solution of diisopropylamine (6.6ml, 0.047 mole) in dry ether (100 ml) at −65° C. under nitrogen was treated with 1.6M n-butyllithium in hexane (26.2ml, 0.042 mole) and the solution stirred for 15 min, before treating with N,N,N',N'-tetramethylethylenediamine (12.3 ml). After stirring for a further 10 min, the solution was treated dropwise over 10 min with a solution of (±) methyl-1-benzyl-3-pyrrolidylcarboxylate (D9, 7.50g, 0.034 mole) in dry ether (20 ml) and stirring continued at −65° C. for 15 min. Ethylene oxide (3.1 g, 0.070 mole) was then bubbled into the solution over 20 min and the mixture was allowed to warm to room temperature over 2h followed by 40 min at reflux. The reaction mixture was treated with saturated sodium hydrogen carbonate solution (50ml) and extracted with ether (3×100 ml). The combined extracts were dried ($Na_2SO_4$) and concentrated in vacuo to leave an orange oil. The unreacted starting material was removed by heating under reflux in 8M hydrochloric acid (50 ml) for 2 h, followed by basifying to saturation with sodium hydrogen carbonate and extraction with ether. The organic extract was dried (Na$_2$SO$_4$) and concentrated in vacuo to leave an orange oil, which was distilled in a Kugelröhr apparatus (b.p. 190°–210° C./0.2–0.5 mmHg) followed by column chromatography on silica gel eluting with ether, to give the title compound (D14) as a pale yellow oil (2.50g, 36%).

Method B

A stirred solution of N-benzyl-N-(methoxymethyl)-N-[(trimethylsilyl)methyl]amine (D11, 160 g of 75% purity, assume 0.51 mole) and α-methylene-γ-butyrolactone (D13, 50 g, 0.51 mole) in dichloromethane (1 1) under nitrogen was cooled to 0° C. and then treated with a 1 M solution of trifluoroacetic acid in dichloromethane (50 ml, 0.05 mole), keeping the temperature below 5° C. The reaction mixture was allowed to warm to room temperature over 2h, then washed with saturated sodium bicarbonate solution. The aqueous wash was extracted with dichloromethane and the organic solutions then combined, washed with brine, dried (Na$_2$SO$_4$) and concentrated in vacuo to leave a pale yellow oil. This was distilled in vacuo to give the title compound (D14) as a colourless oil (96g, 81%) b.p. 160°–170° C. at 1 mmHg.

$^1$H NMR (CDCl$_3$) δ: 1.77–1.92 (1H, m), 2.15–2.40 (3H, m), 2.48–2.78 (3H, m), 2.85–2.98 (1H, m), 3.55–3.70 (2H, m), 4.10–4.30 (2H, m), 7.15–7.35 (5H, m)

DESCRIPTION 15

Ethyl 1-benzyl-1-azoniabicyclo[2.2.1]hept-4 ylcarboxylate bromide (D15)

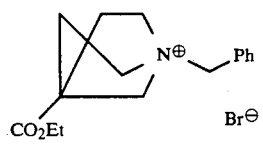

(±) 7-Benzyl-7-aza-2-oxaspiro[4.4]nonan-1-one (D14, 2.5g, 0.012 mole) was treated with a saturated solution of hydrogen bromide in ethanol (150 ml) and the resulting solution allowed to stand at room temperature for 3.5 days. The solution was concentrated in vacuo and the residue basified with saturated potassium carbonate solution, stirred for 10 mins and then extracted with chloroform (3×50ml). The combined extracts were dried (Na$_2$SO$_4$) and concentrated in vacuo to give the title compound (D15) as a beige solid (3.40g, 87%).

DESCRIPTION 16

Ethyl 1-azabicyclo[2.2.1]hept-4-ylcarboxylate (D16)

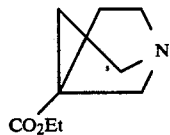

Ethyl 1-benzyl-1-azoniabicyclo[2.2.1]hept-4-ylcarboxylate bromide (D15, 15g, 0.044 mole) in ethanol (250ml) was hydrogenated over 10% Pd on carbon (1g). The reaction was then filtered through celite and the filtrate concentrated in vacuo to yield the crystalline hydrobromide. The salt was partitioned between chloroform and saturated aqueous potassium carbonate solution. The organic phase was separated, dried (Na$_2$SO$_4$), concentrated in vacuo and distilled to give the title compound (D16) as a colourless oil (7.7g, 68%), b.p. 203°–205°/10mmHg.

DESCRIPTION 17

1-Azabicyclo[2.2.1]hept-4-yl-N-methoxy-N-methyl carboxamide (D17)

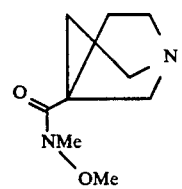

Ethyl 1-azabicyclo[2.2.1]hept-4-ylcarboxylate (D16, 1.75g, 0.01 mole) in concentrated hydrochloric acid (50ml) was heated under reflux for 1.5h. The reaction was then concentrated in vacuo to give a solid which was dissolved in thionyl chloride (30 ml) and heated under reflux for 1.5 h. The mixture was then evaporated to dryness, and freed from residual thionyl chloride by co-evaporation which toluene. The residue was then dissolved in dry acetonitrile (50 ml) and treated with N,O-dimethylhydroxylamine hydrochloride (0.73g, 0.0075 mole) and triethylamine (4.5ml, 0.032 mole). The mixture was stirred overnight at room temperature and then filtered to remove most of the triethylamine hydrochloride. The filtrate was evaporated to dryness and saturated potassium carbonate solution was added. The product was then extracted into chloroform (3×100ml) and the combined extracts were dried (Na$_2$SO$_4$), filtered and evaporated to dryness to give the title compound (D17) as a white solid (0.79g, 41%).

$^1$H-Nmr, 60 MHz (CDCl$_3$) δ: 1.6–2.1 (4H, m), 2.4–3.1 (6H, m), 3.15 (3H, s, N-Me), 3.62 (3H, s, N-OMe).

DESCRIPTION 18

4-Acetyl-1-azabicyclo[2.2.1]heptane (D18)

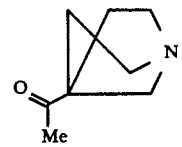

1-Azabicyclo[2.2.1]hept-4-yl-N-methoxy-N-methylcarboxamide (D17, 0.38g, 0.0021 mole) was dissolved in dry tetrahydrofuran (20ml) and cooled to 0° C. under a nitrogen atmosphere. Methyl lithium (1.3ml of a 1.6M solution in ether, 0.0021 mole) was added dropwise with stirring. The mixture was stirred at 0° C. for 1h. A further amount of methyl lithium solution (0.3 ml, 0.0005 mole) was added and the mixture stirred for another 0.5 h. Glacial acetic acid (0.3 ml, 0.005 mole) was added and the mixture evaporated to dryness. The residue was partitioned between saturated potassium carbonate solution and chloroform. The organic layer was dried (Na$_2$SO$_4$) and evaporated to dryness to yield the title compound (D18) (0.3g, 100%) which was used without further purification.

DESCRIPTION 19

4-(α-Bromoacetyl)-1-azabicyclo[2.2.1]heptane hydrobromide (D19)

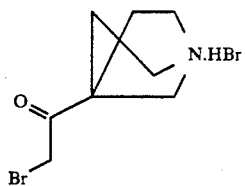

(D19)

The title compound (D19) was prepared from compound D18 using the method outlined in Description 7 (yield=79% after recrystallisation from methanol-ether).

DESCRIPTION 20

(±)exo-Ethyl 1-azabicyclo[2.2.1]hept-3-ylcarboxylate (D20)

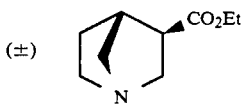

(D20)

(±) exo Ethyl 1-benzyl-1-azoniabicyclo[2.2.1]hept-3-ylcarboxylate hydrobromide (EP A 0257741 Description 9) (54 g, 0.16 mole) was dissolved in ethanol (400 ml) and hydrogenated over 10% Pd-C (8.5 g) at atmospheric pressure and 25° C. After 2 h the solution was filtered and concentrated in vacuo to leave a gum. This was partitioned between chloroform and saturated aqueous potassium carbonate solution and the organic phase separated, dried (Na$_2$SO$_4$) and concentrated in vacuo to leave a gum. This gum was distilled to give the title compound (D20) as a colourless oil (23 g, 85%) b.p. 150° C. at 0.5 mm.

$^1$H Nmr (CDCl$_3$) δ1.10–1.20 (1H,m), 1.25 (3H,t,J=7Hz), 1.54–1.67 (1H,m), 2.15–2.25 (1H,m), 2.28–2.35 (1H,m), 2.38–2.50 (1H,m), 2.60–2.67 (1H,m), 2.70–2.90 (3H,m), 2.93–3.03 (1H,m), 4.13 (2H,q,J=7Hz).

DESCRIPTION 21

(±) exo-1-Azabicyclo[2.2.1]hept-3-yl-N-methyl-N-methoxy carboxamide (D21)

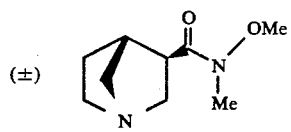

(D21)

(±) exo Ethyl 1-azabicyclo[2.2.1]hept-3-ylcarboxylate (D20) (8.0g, 0.047moles) in hydrochloric acid (5N, 250ml) was heated under reflux for 1.5h. The reaction was then concentrated in vacuo to a solid which was dissolved in thionyl chloride (200ml) and heated under reflux for 0.5h when the copious evolution of sulphur dioxide and hydrogen chloride ceased. The reaction was then concentrated in vacuo to a gum, which was freed from excess thionyl chloride by co-evaporation with toluene. The residue was dissolved in dry acetonitrile (200ml) under an atmosphere of nitrogen and treated with N,O-dimethylhydroxylamine hydrochloride (5g, 0.05 mole). After cooling to 0° C. pyridine (18g, 0.230 mole) was added dropwise. The reaction was allowed to warm to room temperature over a period of 16h. The solvent was then removed in vacuo and the residue partitioned between saturated aqueous potassium carbonate solution and chloroform. The organic phase was separated, dried over sodium sulphate and concentrated in vacuo to a gum, which was distilled in vacuo to afford the title compound (D21) (3.1 g, 36%) Bp 150° C. at 0.1 mmHg.

$^1$H Nmr (CDCl$_3$) δ: 1.2 and 1.6 (each 1H, m, 5-CH$_2$); 2.33 (1H, m, 4-H); 2.5 (2H, m); 2.7–3.0 (5H, m); 3.18 (3H, s, N-CH$_3$); 3.70 (3H, s, O-CH$_3$)

DESCRIPTION 22

(±) exo- and endo-3-Acetyl-1-azabicyclo[2.2.1]heptane (D22)

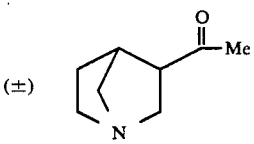

(D22)

A solution of (±) exo 1-azabicyclo[2.2.1]hept-3-yl-N-methyl-N-methoxy carboxamide (D21) (3.10g, 0.168mole) in dry tetrahydrofuran (65ml) was cooled to 0° C. and treated with methyl lithium in hexane (11.1ml, 1.6M, 0.017mole) under an atmosphere of nitrogen for 1.5h. The reaction was then quenched by the addition of acetic acid (3ml) and concentrated in vacuo. The resulting gum was then partitioned between saturated aqueous potassium carbonate solution and chloroform. The organic phase was separated, dried over sodium sulphate and concentrated in vacuo to a gum, which was distilled at 150° C. and 0.2mmHg to afford the title compound (D22) (1.5g, 65%) as 9:1 mixture of exo and endo isomers.

$^1$H Nmr (CDCl$_3$) (signals corresponding to major exo isomer) δ: 1.2 and 1.6 (each 1H, m, 5-CH$_2$); 2.1 (1H, m, 4-CH), 2.18 (3H, s, CH$_3$); 2.2–2.9 (6H, m, 3-CH, 2-CH, 6-CH$_2$, 7-CH$_2$); 3.0 (1H, d,d,d, J=12Hz, 6Hz, 3Hz, 2-CH)

DESCRIPTION 23

(±) exo and endo 3-(α-Bromoacetyl)-1-azabicyclo[2.2.1]heptane hydrobromide (D23)

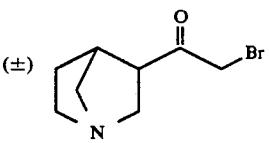

(D23)

A solution of (±) exo and endo 3-acetyl-1-azabicyclo[2.2.1]heptane (D22) (1.07g, 7.7mmol) in dry diethyl ether (75ml) was treated with excess hydrogen bromide gas while cooled in ice. The ether was decanted from the white solid and the solid dissolved in dry methanol (35ml). The solution was cooled to −20° C., treated with bromine (1.23g, 7.7mmole in 10ml of dry methanol) and then left stirring under nitrogen. After 24h and 48h more bromine (0.3g, 1.9mmole each time) was added. After 72 hours distilled water (30ml) was added to the reaction at 0° C. which was then concentrated to a gum whilst kept below 40° C. Trituration with methanol/ether afforded the title compound (D23) as a white solid (0.7g, 30%).

DESCRIPTIONS 24A and 24B (±)5-(α-Aminoacetyl)-1-azabicyclo[3.2.1]octane dihydrochloride salt (D24A) and dihydrobromide salt (D24B)

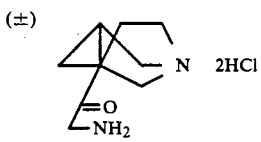

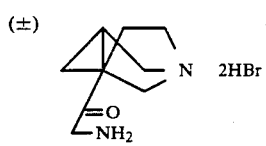

A solution of (±) 5-(α-bromoacetyl)-1-azabicyclo[3.2.1]octane hydrobromide (20.5g, 65.4 mmol) (D5) in dry N,N-dimethylformamide (100 ml) was cooled to 0° C. and sodium azide (10g, 0.15 mol) added with continuous stirring. The reaction mixture was allowed to warm to room temperature over 6h, and then concentrated in vacuo. The residual gum was partitioned between chloroform and saturated aqueous potassium carbonate solution, and the aqueous phase was further extracted with chloroform. Evaporation of the combined organic extracts in vacuo afforded the crude azide which was hydrogenated immediately. A solution of the azide in methanol (200 ml) was treated with concentrated hydrochloric acid (30 ml) and stirred overnight with 10% Pd-C (3g) under an atmosphere of hydrogen. The reaction was filtered through celite and concentrated in vacuo to a gum which crystallised from methanol/ether to afford the title amine dihydrochloride (D24A) as needles (11.31g, 72%).

$^1$H NMR (270 MHz, d$_6$-DMSO) δ: 1.73-2.35 (6H,m), 3.06-3.57 (6H,m), 4.13 (2H,q, CH$_2$NH$_2$).

$^{13}$C NMR (67 MHz, d$_6$-DMSO) δ: 16.3 (CH$_2$), 28.8 (CH$_2$), 29.6 (CH$_2$), 44.4, 49.5, 51.2 (all CH$_2$N), 53.2 (C bridgehead), 57.10 (CH$_2$NH$_2$) and 203.2 (C=O).

Analysis: C$_9$H$_{16}$N$_2$O.2HCl.¼H$_2$O: requires C: 43.99; H: 7.53; N: 11.41, found C: 44.22; H: 7.55; N: 11.30.

A solution of (±) 5-(α-aminoacetyl)-1-azabicyclo[3.2.1]octane dihydrochloride (D24A) (4.7g, 0.02 mol) in a mixture of water (20 ml) and methanol (40 ml) was treated with hydrobromic acid (20 ml of a 48% solution). The mixture was evaporated to dryness under high vacuum to give the title dihydrobromide salt (D24B) (6.3g).

DESCRIPTION 25

(±)5-(2-Chloromethyl-1,3-oxazol-5-yl)-1-azabicyclo[3.2.1]octane hydrochloride (D25)

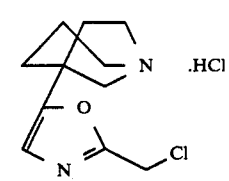

A solution of (±)5-(2-hydroxymethyl-1,3-oxazol-5-yl)-1-azabicyclo[3.2.1]octane (E10) (0.3g, 1.4 mmol) in absolute chloroform (10 ml) under nitrogen, cooled in ice was treated with thionyl chloride (0.31 ml, 4.3 mmole) over 5 minutes. The reaction was allowed to warm up to room temperature over 45 minutes. Evaporation of solvent in vacuo afforded the title compound (D25) as a brown solid (380 mg, 100%) which was used without purification.

$^1$H NMR (CD$_3$OD) δ: 2.02-2.6 (6H,m), 3.3-3.8 (6H,m), 4.70 (2H,s), 7.08 (1H,s).

DESCRIPTION 26

(±)5-(2-Carboxamido-1,3-oxazol-5-yl)-1-azabicyclo[3.2.1]octane (D26)

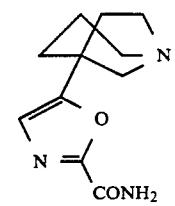

A solution of (±)5-(2-methoxycarbonyl-1,3-oxazol-5-yl)-1-azabicyclo[3.2.1]octane (E9) (0.4g, 1.69 mmole) in methanol (20 ml) was treated with ammonia (5 ml of a 35% aqueous solution) and the mixture was allowed to stand overnight. Evaporation of solvent in vacuo afforded the title compound (D26) as a foam (0.37g, 10%) which was used in the next stage without purification.

DESCRIPTION 27

(±)exo 3-Cyano-1-azabicyclo[3.2.1]octane (D27)

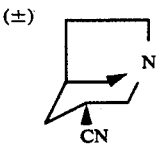

1-Azabicyclo[3.2.1]octan-3-one* (2.7g, 0.022 mole) in dry 1,2-dimethoxyethane (300 ml), under nitrogen, was treated with tosylmethyl isocyanide (3.5g, 0.029 mole) and ethanol (4.6 ml) at 0° C. Potassium t-butoxide (6.8g, 0.06 mole) was added portionwise at such a rate as to be able to maintain the temperature between 5° C. and 10° C. The reaction mixture was allowed to warm to room temperature over 30 min, and then heated at 40° C. for a further 2.5 h. The mixture was cooled and filtered and the residue washed with 1,2-dimethoxyethane. The combined filtrates were concentrated in vacuo and the residual gum purified by column chromatography on alumina eluting with 20% methanol in ethyl acetate. The title compound (D27) was obtained as an oil (2.0g: 66%).

Ir (CN) 2225 cm$^{-1}$.

*D. P. Thill and H. S. Aaron, J. Org. Chem., 1968, 33, 4376.

DESCRIPTION 28

(±)exo-3-Acetyl-1-azabicyclo[3.2.1]octane (D28)

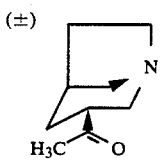

A solution of (±)exo 3-cyano-1-azabicyclo[3.2.1]octane (D27) (1.10g, 0.0081 mole) in dry ether (25 ml) cooled to −10° C. under nitrogen was treated dropwise with methyl lithium (7.1 ml of a 1.6M solution in ether, 0.011 mole). The mixture was stirred at 0° C. for 2h, then cooled to −78° C., and quenched rapidly with 5N sulphuric acid (20 ml). After adjusting the pH to 7-8 with potassium carbonate, the aqueous phase was washed with ether (2×100 ml). The aqueous layer was then saturated with potassium carbonate and extracted exhaustively with chloroform. Concentration of the dried (Na$_2$SO$_4$) extracts afforded a yellow oil (1.1 g) which was purified on neutral alumina using chloroform as eluant. Pooling of pure fractions afforded the title compound (D28) as a colourless oil (0.31g, 23%). Earlier fractions afforded slightly less pure ketone (0.91g, 68%).

Ir (film) 1700 cm$^{-1}$ (υc=o).

$^1$H NMR (CDCl$_3$) δ: 1.60-1.80 (4H, m), 2.10 (3H, s, CH$_3$), 2.32 (1H, m), 2.58 (1H, m), 2.70-3.10 (6H, m).

DESCRIPTION 29

(±) exo 3-(α-Bromoacetyl)-1-azabicyclo[3.2.1]octane hydrobromide salt (D29)

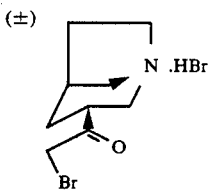

A solution of (±)3-acetyl-1-azabicyclo[3.2.1]octane (D28) (0.29g, 1.9 mmole) in dry diethyl ether (40 ml) was cooled in ice and treated with excess hydrogen bromide gas. After evaporation of solvent in vacuo, the residue was dissolved in dry methanol (40 ml) and treated with bromine (0.3g, 1.9 mmole) at −20° C. The mixture was allowed to warm up to room temperature. After 20h a further quantity of bromine (0.15g, 1 mmole) was added and the reaction left for a further 72h. Distilled water (40 ml) was added to the reaction at 0° C. and after stirring for 1h the mixture was concentrated in vacuo. Trituration of the resulting gum with diethyl ether-methanol afforded the title compound (D29) as a cream solid (0.48g, 80%).

$^1$H NMR (CD$_3$OD) δ: 1.6-1.9 (2H, m), 2.0-2.4 (4H, m), 3.3-3.7 (6H, m), 4.35-4.45 (2H, m).

DESCRIPTIONS 30A and 30B 4-(α-Aminoacetyl)-1-azabicyclo[2.2.1]heptane dihydrochloride salt (D30A) and dihydrobromide salt (D30B)

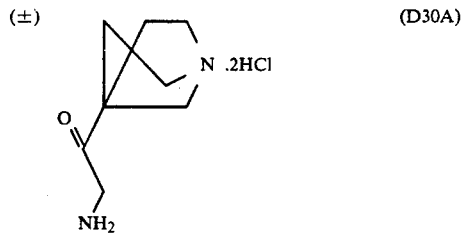

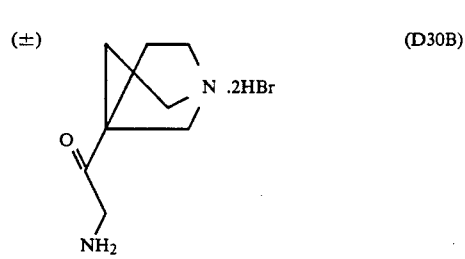

A solution of 4-(α-bromoacetyl)-1-azabicyclo[2.2.1]heptane hydrobromide (D19) (5.2g, 16.5 mmole) in dry N,N-dimethylformamide (25 ml) was cooled to 0° C. under nitrogen and sodium azide (1.61g, 25 mmole) added with continuous stirring. The reaction mixture was allowed to warm to room temperature over 17h, and then concentrated in vacuo. The residual gum was partitioned between chloroform and saturated aqueous potassium carbonate solution, and the aqueous phase was further extracted with chloroform. Evaporation of the combined organic extracts in vacuo afforded the crude azide which was hydrogenated immediately. A solution of the azide in ethanol (30 ml) was treated with concentrated hydrochloric acid (10.5 ml) and stirred for 3h with 10% Pd-C (1g) under an atmosphere of hydrogen. The reaction was filtered through celite and concentrated in vacuo to a gum which was triturated with methanol/ether to afford the title amine dihydrochloride (D30A) as an orange solid (3.4g, 90%).

$^1$H NMR (CD$_3$OD/D$_2$O) δ: 2.23-2.38 (2H, m), 2.37-2.54 (2H, m), 3.38-3.72 (4H, m), 3.56 (2H, s), 4.24 (2H, s).

A solution of 4-(α-aminoacetyl)-1-azabicyclo[2.2.1]heptane dihydrochloride (D30A) (3.43g, 15 mmole) in a mixture of water (25 ml) and methanol (50 ml) was treated with hydrobromic acid (13.7 ml of a 48% solution). The mixture was evaporated to dryness under high vacuum to give the title dihydrobromide salt (D30B) (5.79g).

EXAMPLE 1

(±)
5-(2-Amino-1,3-oxazol-4-yl)-1-azabicyclo[3.2.1]octane
(E1)

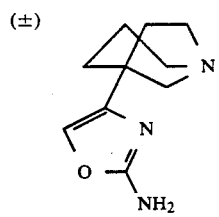

A solution of 5-(α-bromoacetyl)-1-azabicyclo[3.2.1]octane hydrobromide (D5) (0.48g; 1.5mmole) in dry N,N-dimethylformamide (5ml) containing urea (0.14g; 2.3 mmole) was heated under nitrogen to 160° C. (oil bath temperature). The reaction was maintained at this temperature for 15 min. After evaporation of solvent in vacuo the residue was treated with a saturated solution of potassium carbonate (15ml) and then extracted with chloroform (4×20ml). The combined extracts were dried over sodium sulphate and concentrated to give a brown gum. Filtration through a short column of basic alumina using chloroform as eluant, and subsequent trituration with ether-pentane afforded the title compound (E1) as a crystalline solid (0.12g; 41%).

$^1$H Nmr (CDCl$_3$) δ: 1.50 (1H, m), 1.74–1.94 (4H, m), 2.01 (1H, m). 2.74–3.00 (6H, m), 3.15 (1H, m), 4.96 (2H, br,s), 6.85 (1H, s).

Observed mass: 193.1214
Calculated mass for C$_{10}$H$_{15}$N$_3$O: 193.1219

EXAMPLE 2

(±)
3-(2-Amino-1,3-oxazol-5-yl)-1-azabicyclo[2.2.2]octane
(E2)

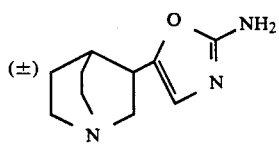

A solution of (±) 3-(α-bromoacetyl-1-azabicyclo[2.2.2]octane hydrobromide (D7) (0.31g; 1.0 mmole in dry N,N-dimethylformamide (3ml) was added dropwise, over a period of 4h, to a stirred solution of monosodium cyanamide (0.13g; 2.0 mmole) in dry N,N-dimethylformamide (10ml). After stirring overnight the reaction was concentrated in vacuo. Repeated co-evaporation with toluene was used to remove remaining N,N-dimethylformamide. The residue was treated with a saturated solution of potassium carbonate (10ml) and extracted into chloroform (4×10ml). The organic layers were dried over sodium sulphate and concentrated to give a crude product consisting mainly of the intermediate cyanamidomethylketone. Passage of this material through a column of basic alumina using a graded eluant of 0-2% methanol in chloroform afforded the title compound (E2) (30mg; 15%).

$^1$H Nmr (CDCl$_3$) δ: 1.33 (1H, m), 1.60 (3H, m), 1.90 (1H, m), 2.65–3.00 (7H, m), 3.12 (1H, m), 4.88 (2H, brs), 6.36 (1H, s).

$^{13}$C Nmr (CDCl$_3$) δ: 21.57, 25.41, 26.86, 33.70, 46.97, 47.49, 51.45, 121.02, 148.35, 159.76.

EXAMPLE 3

(±)
5-(2-Amino-1,3-oxazol-5-yl)-1-azabicyclo[3.2.1]-octane
(E3)

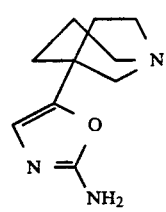

A solution of 5-(α-bromoacetyl)-1-azabicyclo[3.2.1]octane hydrobromide (D5) (3.25g, 0.01mole) in dry N,N-dimethylformamide (40ml) was added dropwise over 4h to a suspension of mono-sodium cyanamide (1.3g, 0.02mole) in dry N,N-dimethylformamide (100ml), stirred under nitrogen. The reaction was stirred for a further fifteen hours and then concentrated in vacuo. The last traces of solvent were removed by co-distillation with toluene (3×30ml). The oily residue was treated with a saturated aqueous solution of potassium carbonate (60ml) and extracted into chloroform (4×60ml). The combined extracts were dried over sodium sulphate and concentrated in vacuo. Purification on basic alumina using a graded eluant of 0-2% methanol in chloroform afforded the title compound (E3) as a white solid (0.4g, 20%) which was converted into the oxalate salt m.p. 191° C. (dec) (from methanol-ether). Oxalate salt:

$^1$H Nmr (d6-DMSO) δ: 1.75–2.25 (6H, m), 3.07–3.54 (6H, m), 5.67 (2H, s), 6.53 (1H, s), 6.62 (2H, brs)

$^{13}$C NMR (d$_6$-DMSO) δ: 17.47, 32.60, 32.83, 41.13, 50.21, 52.19, 60.91, 120.93, 145.47, 160.75, 165.54

EXAMPLE 4

(±5-(2-Amino-1,3-thiazol-4-yl)-1-azabicyclo[3.2.1]octane (E4)

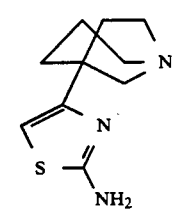

A solution of (±) 5-(α-bromoacetyl)-1-azabicyclo[3.2.1]octane hydrobromide (D5) (3.2g, 0.01mole) in dry N,N-dimethylformamide (10ml) containing thiourea (0.76g, 0.01mole) was heated under nitrogen to 160° C. (oil bath temperature) over a period of 2h. The reaction was maintained at this temperature for 15 min. After concentration of the mixture in vacuo the final traces of solvent were removed by co-distillation with xylene. The residue was diluted with water (30ml) and washed with chloroform (1×30ml). The aqueous layer was saturated with solid potassium carbonate and extracted with chloroform (4×30ml). The combined extracts were dried over sodium sulphate and concentrated in vacuo to give a brown solid (1.5g). Purification on basic alumina using a graded eluant of 0–5% methanol in chloroform followed by crystallisation from methanol-ether afforded a solid (0.38g), m.p. 213.5°–214° C. (dec), which was identified as (±) 5-(2-formamido-1,3-thiazol-4-yl)-1-azabicyclo[3.2.1]octane. This material was dissolved in ethanol and treated with sodium hydroxide solution (5ml of 2.5M NaOH). The mixture was heated under reflux for 3h. After concentration in vacuo the residue was treated with saturated potassium carbonate solution (10ml) and extracted with chloroform (3×10ml). The combined extracts were dried over sodium sulphate and concentrated in vacuo to give the title compound (E4) as a crystalline solid (0.28g, 13%) which was converted into the oxalate salt. Oxalate salt:

$^1$H Nmr (d$_6$-DMSO) δ: 1.7–2.3 (6H, m), 3.0–3.45 (6H, m), 6.33 (1H, s), 7.06 (2H, s)

$^{13}$C Nmr (d$_6$-DMSO) δ: 18.12, 33.98, 34.13, 48.60, 50.63, 52.50, 62.13, 99.74, 154.80, 165.5, 168.25

EXAMPLE 5

2-Amino-1,3-oxazol-5-yl)-1-azabicyclo[2.2.1]heptane (E5)

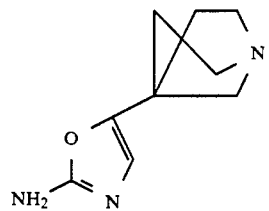

(E5)

4-(α-Bromoacetyl)-1-azabicyclo[2.2.1]heptane hydrobromide (D19) was converted into the title compound (E5) by the procedure outlined in Example 2. The oxalate salt was obtained as a pale yellow crystalline solid (0.14g; 13%), m.p. 191°–195° C. Oxalate salt:
$^1$H Nmr (d$_6$-DMSO) δ: 1.93–2.08 (2H, m), 2.20–2.34 (2H, m), 3.30 (2H, s), 3.35–3.47 (2H, m), 3.52–3.65 (2H, m), 5.30–6.30 (2H, brs), 6.71 (1H, s), 6.73 (2H, s).

$^{13}$C Nmr (d$_6$-DMSO) δ: 31.39, 44.26, 52.08, 60.53, 123.10, 140.33, 161.20, 164.54

EXAMPLE 6

(±) exo and endo
3-(2-Amino-1,3-oxazol-5-yl)-1-azabicyclo[[2.2.1]heptane (E6)

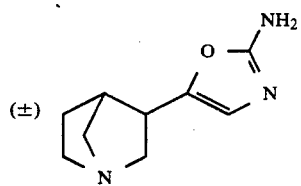

(E6)

A solution of (±) exo and endo 3-(α-bromoacetyl)-1-azabicyclo[2.2.1]heptane hydrobromide (D23) (0.7g, 2.3mmole) in dry N,N-dimethylformamide (10ml) was added dropwise over four hours to a suspension of mono-sodium cyanamide (0.3g, 4.7mmole) in dry N,N-dimethylformamide (22ml) under nitrogen. The reaction was left stirring for a further 15h. After evaporation of the solvent in vacuo the residue was treated with a saturated aqueous solution of potassium carbonate (27ml) and then extracted with chloroform (4×27ml). The combined extracts were dried over sodium sulphate and concentrated in vacuo. The residue was chromatographed on basic alumina in a gradient of 0–2% methanol in chloroform. This afforded the title compound (E6) as a white solid (30mg, 7%), consisting of a 4:1 mixture of exo and endo isomers.

$^1$H Nmr (CDCl$_3$) (Signals corresponding to major exo isomer) δ:
1.21 (1H, m), 1.52 (1H, m), 2.17–3.05 (8H, m), 5.04 (2H, s), 6.16 (1H, s)

$^{13}$C Nmr (CDCl$_3$) (Signals corresponding to major exo isomer) δ:
29.65, 39.29, 41.72, 53.45, 57.71, 59.42, 120.15, 147.54, 159.74

EXAMPLE 7

(±)
3-(2-Amino-1,3-thiazol-4-yl)-1-azabicyclo[2.2.2]octane (E7)

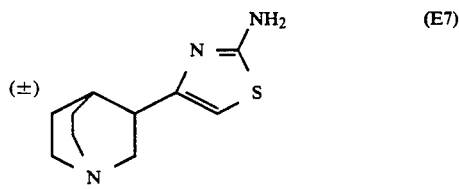

(E7)

A solution of (±) 3-(α-bromoacetyl)-1-azabicyclo[2.2.2]octane hydrobromide (D7) (1.0g, 3.2mmole) in dry N,N-dimethylformamide (3ml) containing thiourea (0.24g, 3.2mmole) was heated under nitrogen to 110° C. (oil bath temperature). The reaction was maintained at this temperature for 10 min. After evaporation of solvent in vacuo the residue was treated with saturated solution of potassium carbonate (20ml) and then extracted with chloroform (5×20ml). The combined extracts were dried over sodium sulphate and concentrated to give an orange solid. This was chromotographed on basic alumina, eluting with 0–2% methanol in chloroform, and afforded the title compound (E7) as a white solid (0.21g, 32%).

$^1$H Nmr (d$_6$-DMSO) δ: 1.24 (1H, m), 1.58 (3H, m), 1.93 (1H, m), 2.54–3.09 (7H, m), 6.22 (1H, s), 6.82 (2H, s)

$^{13}$C Nmr (d$_6$-DMSO) δ: 21.44, 26.07, 27.38, 38.20, 46.72, 47.16, 52.13, 99.60, 154.82, 167.84.

EXAMPLE 8

(±)
3-(2-Amino-1,3-oxazol-4-yl)-1-azabicyclo[2.2.2]octane (E8)

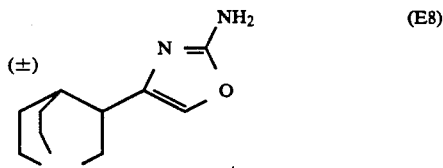

(E8)

A solution of (±) 3-(α-bromoacetyl)-1-azabicyclo[2.2.2]octane hydrobromide (D7) (1.0g, 3.2mmole) in dry N,N-dimethylformamide (3ml) containing urea (0.29g, 4.8mmole) was heated under nitrogen to 110° C. (oil bath temperature). The reaction was maintained at this temperature for 10 min. After evaporation of the solvent in vacuo the residue was treated with a saturated solution of potassium carbonate (25ml) and then extracted with chloroform (4×20ml). The combined extracts were dried over sodium sulphate and concentrated to give an orange gum. This was chromotographed on basic alumina eluting with 0-2% methanol in chloroform. This afforded the title compound (E8) as a white solid (0.13g, 20%).

¹H Nmr (d₆-DMSO) δ: 1.25 (1H, m), 1.57 (3H, m), 1.85 (1H, m), 2.52-2.83 (6H, m), 2.94-3.06 (1H, m), 6.46 (2H, s), 7.17 (1H, s)

¹³C Nmr (D₆-DMSO) δ: 21.36, 25.47, 27.15, 33.90, 46.70, 47.11, 51.79, 126.50, 142.53, 161.17.

EXAMPLE 9

(±)5-(2-Methoxycarbonyl-1,3-oxazol-5-yl)-1-azabicyclo [3.2.1]octane (E9)

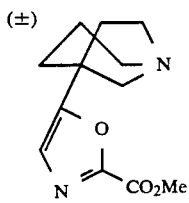

A stirred suspension of (±) 5-(α-aminoacetyl)-1-azabicyclo[3.2.1]octane dihydrobromide salt (D24B) (2.74g, 8.3 mmole) in absolute chloroform (100 ml) and dry acetonitrile (50 ml) was treated dropwise under nitrogen with methyl oxalyl chloride (2.3 ml, 25mmole). Dry pyridine (13.5 ml, 170 mmole) was added dropwise over a period of 2h. A further portion of oxalyl chloride (0.75 ml, 8.3 mmole) was added, and the reaction was stirred for a further 17h. The reaction was quenched with ice and treated with a saturated solution of potassium carbonate (25 ml). The organic layer was separated and the aqueous phase extracted with chloroform (2×25 ml). The combined organic layers were dried over sodium sulphate then concentrated in vacuo. Rapid filtration through a short column of neutral alumina in a gradient of 0-0.5% methanol in chloroform afforded the title compound (E9) as a gum (0.93g, 47%).

¹H nmr (CDCl₃) δ: 1.4-2.1 (6H,m), 2.7-3.0 (6H,m), 3.92 (3H,s), 6.91 (1H,s).

Hydrochloride salt m.p. 168°-170° C. (from methanol-ether).

Analysis: $C_{12}H_{17}N_2O_3$: requires C: 52.85; H: 6.28; N: 10.27, found C: 52.63; H: 6.23; N: 9.82.

EXAMPLE 10

(±)5-(2-Hydroxymethyl-1,3-oxazol-5-yl)-1-azabicyclo [3.2.1]octane (E10)

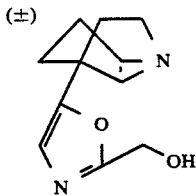

A solution of (±)5-(2-methoxycarbonyl-1,3-oxazol-5-yl)-1-azabicyclo[3.2.1]octane (E9) (0.2g, 0.8 mmole) in dry toluene (12 ml), cooled in ice, under nitrogen, was treated with diisobutylaluminium hydride (1.04 ml of a 1.5M solution in toluene, 1.6 mmole) over 15 min. The reaction was allowed to warm up to room temperature over 1h, then more diisobutylaluminium hydride (1.6 mmole) was added and the reaction left for a further 1h. After quenching with methanol (8 ml) and 10% sodium hydroxide solution (10 ml), potassium carbonate was added until the aqueous layer was saturated. The organic layer was separated and the aqueous phase was extracted with chloroform. The combined organic layers were dried over sodium sulphate 9 then concentrated in vacuo. Purification of the residue on neutral alumina in a gradient of 0-5% methanol in chloroform afforded the title compound (E10) as a gum (0.1g, 55%) which was converted into the hydrochloride salt m.p. 152° C. (dec.) (from methanol-ether).

Hydrochloride salt:

¹H Nmr (d₆-DMSO) δ: 1.8-2.3 (6H,m), 3.1-3.6 (6H,m), 4.45 (2H,s), 7.0 (1H,s).

¹³C Nmr (d₆-DMSO) δ: 16.52, 31.62, 31.82, 41.34, 49.62, 51 22, 55.83, 59.12, 122.16, 152.56, 162.94.

EXAMPLE 11

(±)5-(2-Methoxymethyl-1,3-oxazol-5-yl)-1-azabicyclo [3.2.1]octane (E11)

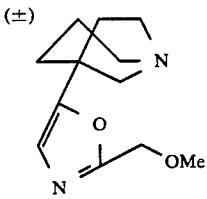

A solution of (±)5-(2-chloromethyl-1,3-oxazol-5-yl)-1-azabicyclo[3.2.1]octane hydrochloride (D25) (75 mg, 0.28 mmole) in dry methanol (2 ml) was added dropwise over 2h to a solution of sodium methoxide in methanol (15 ml of a 25 wt % solution, 66 mmole), under nitrogen, cooled in ice. After evaporation of the solvent in vacuo the residue was treated with saturated aqueous potassium carbonate solution (10 ml) and extracted with chloroform. The combined extracts were dried over sodium sulphate then concentrated in vacuo. The residue was chromatographed on neutral alumina in a gradient of 0-0.5% methanol in chloroform. This afforded the title compound (E11) as an oil (50 mg, 79%) which was converted into the hydrochloride salt m.p. 129°-131° C. (from acetone-ether).

Hydrochloride salt:

¹H Nmr (d₆-DMSO) δ:

1.8-2.3 (6H,m), 3.1-3.6 (6H,m), 3.29 (3H,s), 4.44 (2H,s), 7.07 (1H,s).

¹³C Nmr (d₆-DMSO) δ: 16.49, 31.53, 31.77, 41.33, 49.62, 51.22, 57.98, 59.07, 65.44, 122.42, 153.22, 160.00

Analysis: $C_{12}H_{19}ClN_2O_2$: requires C: 55.70; H: 7.40; N: 10.83, found C: 55.66; H: 7.41; N: 10.69.

EXAMPLE 12

(±)5-(2-Fluoromethyl-1,3-oxazol-5-yl)-1-azabicyclo[3.2.1]octane (E12)

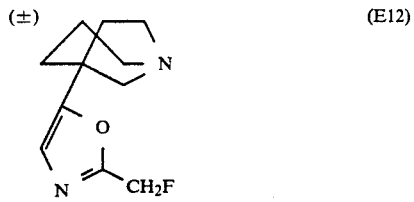

Sodium monofluoroacetate (110mg, 1.1 mmole) was dissolved in dry, distilled N,N-dimethylformamide (20ml), the solution cooled to −15° C., and N-methylmorpholine (0.114ml, 1.0 mmole) added, followed by isobutylchloroformate (0.176ml, 1.1 mmole). The resulting white suspension was stirred for 2-3 minutes. 5-(2-Aminoacetyl)-1-azabicyclo[3.2.1]octane dihydrochloride salt (D24A) (250mg, 1.0 mmol) was suspended in dry N,N-dimethylformamide (20ml) and N-methylmorpholine (0.228ml, 2.0 mmol) added. The resulting suspension was added immediately to the reaction mixture, the suspension stirred for 15-30 min and then allowed to warm to room temperature and stirred for 90 min. The reaction mixture was evaporated to dryness under reduced pressure and polyphosphoric acid (20g) added. The mixture was heated with stirring at 160° C. for 30 minutes and the warm syrup was then poured carefully onto a mixture of solid potassium carbonate and ice. The resulting aqueous solution was saturated with solid potassium carbonate and extracted with ethyl acetate (3×250ml) and chloroform (2×250ml). The organic extracts were dried ($Na_2SO_4$), filtered, combined and evaporated to dryness under reduced pressure. The resulting brown oil which was purified by column chromatography (basic alumina eluting with diethyl ether) to yield a pale yellow oil (37mg, 18%), which was converted into the hydrochloride salt m.p. 138°-141° C. (ethyl acetate).

$^1$H NMR ($d_6$-DMSO) 2.05-2.55 (6H, m), 3.32-3.85 (6H, m), 5.57 and 5.75 (each 1H, s, $CH_2F$) and 7.42 (1H, s, oxazole CH).

Observed mass=210.0826. Calculated mass for $C_{11}H_{15}FN_2O$=210.0800

EXAMPLE 13

(±)5-(2-Cyano-1,3-oxazol-5-yl)-1-azabicyclo[3.2.1]octane (E13)

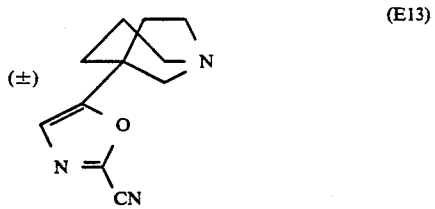

A suspension of (±)5-(2-carboxamido-1,3-oxazol-5-yl)-1-azabicyclo[3.2.1]octane (D26) (0.37g, 1.69 mmole) in a mixture of dry tetrahydrofuran (30 ml) and dry pyridine (10 ml) was cooled in ice and treated dropwise with trifluoroacetic anhydride (0.3 ml, 2.1 mmole). The resulting clear yellow solution was stirred at ice temperature for a further 1.5h. After concentration in vacuo the residue was treated with cold saturated aqueous potassium carbonate (10 ml) and extracted with chloroform (4×15 ml). Concentration of the dried ($Na_2SO_4$) organic layers followed by filtration through a short neutral alumina column using a graded eluant of 0.05%-0.8% ethanol in chloroform afforded the title compound (E13) as an oil (0.15g, 44%) which was converted into the hydrochloride salt m.p. 213°-215.5° C. (from methanol-ether).

Hydrochloride salt:
$^1$H NMR ($d_6$-DMSO) δ: 1.80-2.45 (6H, m), 3.15-3.65 (6H, m), 7.60 (1H, s).
$^{13}$C NMR ($d_6$-DMSO) δ: 16.72, 31.73, 31.78, 41.97, 49.81, 51.38, 59.11, 109.58, 125.70, 135.63, 157.83.

Analysis: $C_{11}H_{14}ClN_3O$: requires C:55.12; H:5.89; N:17.53, found C:54.68; H:5.89; N:17.20.

EXAMPLE 14

(±)5-(2-Acetylamino-1,3-oxazol-5-yl)-1-azabicyclo[3.2.1]octane (E14)

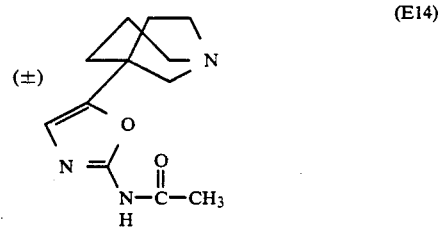

A solution of (±)5-(2-amino-1,3-oxazol-5-yl)-1-azabicyclo[3.2.1]octane (E3) (0.25g, 1.3 mmole) in acetic anhydride (8 ml) was refluxed for 1h under nitrogen. The reaction mixture was concentrated in vacuo and the residue treated with saturated aqueous potassium carbonate solution (10 ml). After extraction into chloroform (3×10 ml) the organic extracts were dried over sodium sulphate and concentrated in vacuo. Trituration of the resulting gum with ether afforded the title compound (E14) as a solid (180 mg, 60%) m.p. 142°-143° C. (from methanol-ether).

$^1$H NMR ($CDCl_3$) δ: 1.55-2.57 (6H, m), 1.94 (3H, s), 2.64-3.28 (6H, m), 6.63 (1H, s).

EXAMPLE 15

(±)5-(2-Methylamino-1,3-oxazol-5-yl)-1-azabicyclo[3.2.1]octane (E15)

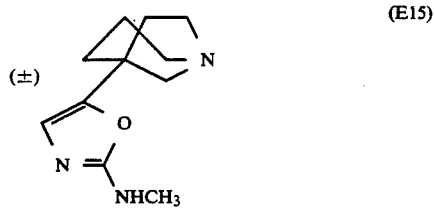

A solution of (±)5-(2-amino-1,3-oxazol-5-yl)-1-azabicyclo[3.2.1]octane (E3) (0.2g, 1 mmole) in dry tetrahydrofuran (10 ml) was treated with di-t-butyl dicarbonate (0.24g, 1.1 mmole) then stirred under nitrogen for 1h. The reaction mixture was concentrated in vacuo, treated with saturated aqueous potassium carbonate solution (10 ml) then extracted into chloroform (3×10 ml). The combined organic extracts were dried over sodium sulphate then concentrated in vacuo to a gum which was dissolved in dry diethyl ether (5 ml) then treated with benzyl bromide (0.18g, 1 mmole). After stirring for 17h under nitrogen, the supernatant was removed and the residual white solid washed with ether and dried in vacuo. A solution of this material in dry N,N-dimethylformamide was treated with sodium hydride (24 mg, 1.0 mmole) and heated at 40° C. until the evolution of hydrogen ceased. Methyl p-toluenesulphonate (146 mg, 0.78 mmole) was added and the mixture was heated to 50° C. After 8h additional quantities of sodium hydride (12 mg) and methyl p-toluenesulphonate (73 mg) were added and the reaction was heated at 50° C. for 19h. Concentration in vacuo followed by trituration with ether afforded a yellow solid which was dissolved in ethanol, treated with 10% Palladium on charcoal (0.04g) and acetic acid (43 mg, 0.71 mmole) then stirred under hydrogen for 1h. The reaction mixture was filtered through celite, then concentrated in vacuo to a gum which was treated with saturated aqueous potassium carbonate (20 ml) and extracted into chloroform (3×25 ml). The combined organic extracts were dried over sodium sulphate then concentrated in vacuo. Chromatography on neutral alumina in a gradient of 0–2% methanol in chloroform afforded the faster running component as a gum which was dissolved in dry dichloromethane (5 ml) and treated with anisole (70 mg, 0.65 mmole) followed by trifluoroacetic acid (0.3, 2.6 mmole) at 0° C. After stirring at room temperature for 1.75 h the solvent was removed in vacuo, the residue was dissolved in water and washed with pentane (5×25 ml). The aqueous layer was basified with potassium carbonate and extracted into chloroform (3×20 ml). The organic extracts were dried over sodium sulphate then concentrated in vacuo. The residue was chromatographed on basic alumina in a gradient of 0–2% methanol in chloroform to afford the title compound (E15) as a clear gum (8 mg).

$^1$H Nmr (CDCl$_3$) δ: 1.43–2.18 (6H, m), 2.7–3.3 (6H, m), 2.96 (3H, s), 4.61 (1H, brs), 6.38 (1H, s).

Observed mass: 207.1371. Calculated mass for C$_{11}$H$_{17}$N$_3$O=207.1373.

EXAMPLE 16

(±) exo 3-(2-Amino-1,3-oxazol-5-yl)-1-azabicyclo[3.2.1]octane (E16)

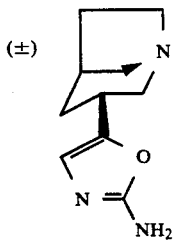

A solution of (±)3-(α-bromoacetyl)-1-azabicyclo[3.2.1]octane hydrobromide (D29) (0.48g, 1.5 mmole) in dry N,N-dimethylformamide (8 ml) was added to a solution of mono-sodium cyanamide (0.2g, 3.1 mmole) over 4h under nitrogen. The reaction was stirred for a further 17h, then concentrated in vacuo. The last traces of N,N-dimethylformamide were removed by codistillation with toluene (3×10 ml). The residue was treated with saturated potassium carbonate solution (30 ml) then extracted into chloroform (3×30 ml). The combined chloroform extracts were dried using sodium sulphate and concentrated in vacuo. The residue was chromatographed on basic alumina in a gradient of 0–2% methanol in chloroform to afford the title compound (E16) as a white solid (30 mg, 10%) m.p. 169°–174° C. (from isopropanol-light petrol).

$^1$H Nmr (CDCl$_3$) δ: 1.52–1.94 (4H, m), 2.28–2.40 (1H, m), 2.55–3.09 (7H, m), 4.77 (2H, s), 6.30 (1H, s).

EXAMPLE 17

4-(2-Methoxymethyl-1,3-oxazol-5-yl)-1-azabicyclo[2.2.1]-heptane (E17)

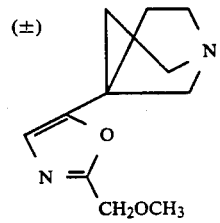

A stirred suspension of 4-(α-aminoacetyl)-1-azabicyclo[2.2.1]heptane dihydrobromide salt (D30B) (0.32g, 1.0 mmole) in a mixture of absolute chloroform (30 ml) and dry acetonitrile (10 ml) was cooled in ice, under nitrogen and treated with methoxyacetyl chloride (0.18 ml, 2.0 mmole). 2,6-Lutidine (2.3 ml, 20 mmole) was added dropwise over 4.5h and the mixture was kept overnight at 0° C. The reaction was quenched with ice followed by a saturated aqueous solution of potassium carbonate (15 ml). The aqueous phase was extracted with chloroform (4×30 ml) and the combined organic layers were dried (Na$_2$SO$_4$) and concentrated in vacuo to give a brown oil (0.18g) which was mixed with polyphosphoric acid (8g) and placed in an oil bath at 120° C. The temperature was raised to 160° C. over 9 min and stirring was continued at this temperature for 15 min. The cooled reaction mixture was quenched with ice and neutralised at ice temperature with 40% aqueous sodium hydroxide. After saturation with potassium carbonate the solution was extracted with chloroform (4×25 ml). The combined organic layers were dried (Na$_2$SO$_4$) and concentrated in vacuo. Purification on neutral alumina using 0.5% methanol in chloroform as eluant afforded the title compound (E17) as a pale yellow oil (60 mg, 29%) which was converted into the hydrochloride salt m.p. 145°–146.5° C. (from acetone-ether).

Hydrochloride salt:
$^1$H Nmr (d$_6$-DMSO) δ: 2.18 (2H, m), 2.42 (2H, m), 3.47 (3H, s), 3.47–3.80 (6H, m), 4.62 (2H, s), 7.34 (1H, s).
$^{13}$C Nmr (d$_6$-DMSO) δ: 31.33, 44.18, 51.88, 58.03, 60.07, 65.45, 123.95, 149.55, 160.39.

Analysis: C$_{11}$H$_{17}$ClN$_2$O$_2$.¼H$_2$O: requires: C:53.01; H:6.98; N:11.24, found : C:52.80; H:6.85; N:10.90.

BIOLOGICAL ACTIVITY

Radio ligand Binding

Cerebral cortex from Hooded Lister rats (Olac, UK) is homogenised in 2.5 vols ice-cold 50mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1ml aliquots at −20° C.

Incubations (total volume 2ml) are prepared using the above buffer with the addition of 2mM magnesium chloride in the 3H-Oxotremorine-M (3H-OXO-M) experiments. For 3H-Quinuclidinyl Benzilate (3H-QNB), 1ml of stored membranes is diluted to 30ml and 0.1 ml mixed with test compound and 0.27nM (c. 25,000 cpm) 3H-QNB (Amersham International). For 3H-OXO-M, 1ml of membranes is diluted to 6ml and 0.1 ml mixed with test compound and 2nM (c. 250,000 cpm) 3H-OXO-M (New England Nuclear).

Non-specific binding of 3H-QNB is defined using 1μM Atropine sulphate (2μM Atropine) and of 3H-OXO-M using 10μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4ml ice-cold buffer. Radioactivity is assessed using a Packard BPLD scintillation counter, 3ml Pico-Fluor 30 (Packard) as scintillant.

This test provides an indication of the muscarinic binding activity of the test compound. The results are obtained as $IC_{50}$ values (i.e. the concentration which inhibits binding of the ligand by 50%) for the displacement of the muscarinic agonist 3H-OXO-M and the muscarinic antagonist 3H-OXO-M) gives an indication of the agonist character of the compound. Agonists typically exhibit a large ratio; antagonists typically exhibit a ratio near to unity.

The results are shown in Table 1:

TABLE 1

| Compound | [³H]—OXO—M $IC_{50}$ (nm) | [³H]—QNB $IC_{50}$ (nm) |
|---|---|---|
| E1+ | 250 | 42000 |
| E2++ | 440 | 17000 |
| E3++ | 4 | 3500 |
| E4++ | 280 | 5600 |
| E5++ | 18 | 11000 |
| E6++ | 200 | 10300 |
| E9+ | 2000 | 30463 |
| E10+ | 206 | 7000 |
| E11+ | 220 | 2600 |
| E12+ | 5 | 440 |
| E13+ | 380 | 2800 |
| E16 | 560 | 42000 |
| E17+ | 1050 | 60000 |

+Tested as the hydrochloride salt
++Tested as the oxalate salt

I claim:

1. A compound of formula (I) or a pharmaceutically acceptable salt thereof:

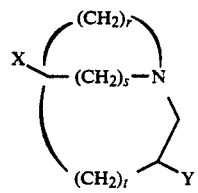

(I)

in which one of X and Y represents hydrogen and the other represents Z, where Z is a group

in which Q represents a 3-membered divalent residue completing a 5-membered aromatic ring and comprises one heteroatom selected from oxygen, nitrogen and sulphur any amino nitrogen being optionally substituted by a $C_{1-2}$ alkyl, and at least one ring carbon atom being substituted by a group $R_1$; or a group

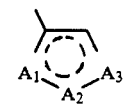

in which $A_1$, $A_2$ and $A_3$ complete a 5-membered aromatic ring and $A_1$ is oxygen or sulphur, $A_2$ is $CR_2$ and $A_3$ is nitrogen or CH, or $A_2$ is oxygen or sulphur, $A_1$ is CH and $A_3$ is $CR_2$; and $R_1$ and $R_2$ are selected from, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, $C_{2-4}$ alkenyl, $C_{2-4}$ alkynyl or $C_{1-2}$ alkyl substituted with $OR_4$, $N(R_4)_2$, $SR_4$, $CO_2R_4$, $CON(R_4)_2$ or one, two or three halogen atoms, in which each $R_4$ is independently hydrogen or $C_{1-2}$ alkyl and $R_5$ is $OR_4$, $NH_2$ or $NHR'_4$; r represents an integer of 2 or 3, s represents an integer of 1 or 2 and t represents 0 or 1, with the proviso that when Y is hydrogen s is 1.

2. A compound according to claim 1 wherein the 5-membered aromatic ring is selected from 1,3-oxazol-4-yl, 1,3-oxazol-5-yl, 1,2-oxazol-3-yl and 1,3-thiazol-4-yl.

3. A compound according to claim 1 wherein $R_1$ and $R_2$ are selected from $NH_2$, $CH_2F$, $CO_2CH_3$, $CH_2OH$, $CH_2OCH_3$, CN, $NHCOCH_3$ and $NHCH_3$.

4. A compound according to claim 1 wherein Z is selected from 2-amino-1,3-oxazol-4-yl, 2-amino-1,3-oxazol-5-yl, 2-amino-1,3-thiazol-4-yl, 2-fluoromethyl-1,3-oxazol-5-yl, 2-methoxycarbonyl-1,3-oxazol-5-yl, 2-hydroxymethyl-1,3-oxazol-5-yl, 2-methoxymethyl-1,3-oxazol-5-yl, 2-cyano-1,3-oxazol-5-yl, 2-methylcarbonylamino-1,3-oxazol-5-yl and 2-methylamino-1,3-oxazol-5-yl.

5. A compound according to claim 1 wherein Y is hydrogen.

6. (±) 5-(2-Amino-1,3-oxazol-4-yl)-1-azabicyclo[3.2.1]octane,
   (±) 5-(2-amino-1,3-oxazol-5-yl)-1-azabicyclo[3.2.1]octane,
   (±) 5-(2-amino-1,3-thiazol-5yl)-1-azabicyclo[3.2.1]octane,
   (±) 5-(2-methoxycarbonyl-1,3-oxazol-5-yl)-1-azabicyclo[3.2.1]octane,
   (±) 5-(2-hydroxymethyl-1,3-oxazol-5-yl)-1-azabicyclo[3.2.1]octane,
   (±) 5-(2-methoxymethyl-1,3-oxazol-5-yl)-1-azabicyclo[3.2.1]octane,
   (±) 5-(2-fluoromethyl-1,3-oxazol-5-yl)-1-azabicyclo[3.2.1]octane,
   (±) 5-(2-cyano-1,3-oxazol-5-yl)-1-azabicyclo[3.2.1]octane,
   (±) 5-(2-acetylamino-1,3-oxazol-5-yl)-1-azabicyclo[3.2.1]octane, (±) 5-(2-methylamino-1,3-oxazol-5-yl)-1-azabicyclo[3.2.1]octane,
(±) exo 3-(2-amino-1,3-oxazol-5-yl)-1-azabicyclo[3.2.1]octane,
or a pharmaceutically acceptable salt of any of the said compounds.

7. A pharmaceutical composition which comprises a compound of formula (I) as defined in claim 1 or a pharmaceutically acceptable salt thereof, and a pharmaceutically acceptable carrier.

8. A method of treatment and/or prophylaxis of dementia in mammals including humans, which comprises administering to the sufferer an effective amount of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 5,166,357

DATED : November 24, 1992

INVENTOR(S) : Barry S. Orlek, et al.

It is certified that error appears in the above-identified patent and that said Letters Patent is hereby corrected as shown below:

Claim 1, at column 36, lines 31-33, delete "r represents an integer of 2 or 3, s represents an integer of 1 or 2 and t represents 0 or 1, with the proviso that when Y is hydrogen s is 1" and replace with —wherein (r,s,t) is (3,1,0) or (2,1,1)—.

Signed and Sealed this

Seventh Day of December, 1993

Attest:

BRUCE LEHMAN

*Attesting Officer*  *Commissioner of Patents and Trademarks*